US011351155B2

(12) United States Patent
Stamler

(10) Patent No.: US 11,351,155 B2
(45) Date of Patent: Jun. 7, 2022

(54) COMPOSITIONS AND METHODS OF MODULATING S-NITROSYLATION

(71) Applicant: CASE WESTERN RESERVE UNIVERSITY, Cleveland, OH (US)

(72) Inventor: Jonathan Stamler, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 15/533,268

(22) PCT Filed: Dec. 7, 2015

(86) PCT No.: PCT/US2015/064308
§ 371 (c)(1),
(2) Date: Jun. 5, 2017

(87) PCT Pub. No.: WO2016/090373
PCT Pub. Date: Jun. 9, 2016

(65) Prior Publication Data
US 2017/0360755 A1 Dec. 21, 2017

Related U.S. Application Data

(60) Provisional application No. 62/088,002, filed on Dec. 5, 2014.

(51) Int. Cl.
A61K 31/4184 (2006.01)
A61P 9/10 (2006.01)
A61K 45/06 (2006.01)
A61K 31/433 (2006.01)
A61K 31/145 (2006.01)
A61K 31/423 (2006.01)
A61K 31/403 (2006.01)
A61K 31/675 (2006.01)

(52) U.S. Cl.
CPC ........ A61K 31/4184 (2013.01); A61K 31/145 (2013.01); A61K 31/403 (2013.01); A61K 31/423 (2013.01); A61K 31/433 (2013.01); A61K 31/675 (2013.01); A61K 45/06 (2013.01)

(58) Field of Classification Search
CPC .............................. A61K 31/4184; A61P 9/10
See application file for complete search history.

(56) References Cited

U.S. PATENT DOCUMENTS

| 2,683,718 | A | | 7/1954 | Dornfeld et al. | |
|---|---|---|---|---|---|
| 4,436,745 | A | * | 3/1984 | York, Jr. .............. | C07D 235/02 514/389 |
| 5,153,211 | A | | 10/1992 | York, Jr. | |
| 7,674,795 | B2 | | 3/2010 | Mailliet et al. | |
| 2007/0232527 | A1 | | 10/2007 | Ghosal et al. | |
| 2009/0270490 | A1 | | 10/2009 | Srivastava et al. | |
| 2010/0292178 | A1 | | 11/2010 | Young | |
| 2011/0092566 | A1 | | 4/2011 | Srivastava et al. | |
| 2014/0206693 | A1 | | 7/2014 | Srivastava et al. | |

FOREIGN PATENT DOCUMENTS

| EP | 1961420 A1 | 8/2008 |
|---|---|---|
| EP | 1987829 A1 | 11/2008 |
| WO | 2002/47680 A2 | 6/2002 |
| WO | 2004/110488 A1 | 12/2004 |
| WO | 2009/076580 A2 | 6/2009 |
| WO | 2009/076580 A2 | 6/2009 |
| WO | 2010/104595 A1 | 9/2010 |
| WO | 2016090373 A1 | 6/2016 |

OTHER PUBLICATIONS

Kevil et al. Curr. Opin. Investig. Drugs, 2010, vol. 11. No. 10, pp. 1127-1134.*
Hwang et al. The FASEB Journal, Published online Dec. 2001, pp. 1-22.*
Supplemental European search report for application No. 15864966.5-1112/3226859, dated Nov. 30, 2018.
European Search Report for application No. 15864966.5-1112/3226859.
Tao B et al.: "Synthesis of Conformationally Constrained Spirohydantoins With a Dibenzoaa,D0heptadiene Ring", Synthesis, Georg Thieme Verlag, Stuttgart, DE, No. 10, Feb. 29, 2000, pp. 1449-1453.
Partial Supplementary European Search Report for Application No. 15864966.5-1112/3226859.
Puneet Anand, "Purification and Characterization of Novel Denitrosylases from Yeast and Mammals", Dec. 31, 2012, pp. 1-156.
Puneet Anand et al., "Identification of S-nitroso-CoA reductases that regulate protein S-nitrosylation", Proceedings of the National Academy of Sciences, vol. 111, No. 52, Dec. 15, 2014, pp. 18572-18577.
Applicant: Case Western Reserve University; Compositions and Methods of Modulating S-Nitrosylation; European Patent Application No. 15864966.5; European Office Action dated Feb. 18, 2021; 7 pgs.
Applicant: Case Western Reserve University; PCT International Application No. PCT/US19/52426, Filed: Sep. 23, 2019; PCT International Search Report and Written Opinion, Authorized Officer: Lee Young; dated Feb. 7, 2020; 9 pgs.
PubChem—CID—10335836, Create Date: Oct. 25, 2006; p. 2.

* cited by examiner

Primary Examiner — Samira J Jean-Louis
(74) Attorney, Agent, or Firm — Tarolli, Sundheim, Covell & Tummino LLP

(57) ABSTRACT

A method of treating disorders associated with NO/SNO deficiency or benefiting from increased SNO in a subject in need thereof includes administering to the subject an ADH inhibitor, AKR inhibitor, SNO-CoAR inhibitor, and/or SNO-CoA at an amount(s) effective to promote S-nitrosylation of proteins in the subject.

7 Claims, 5 Drawing Sheets

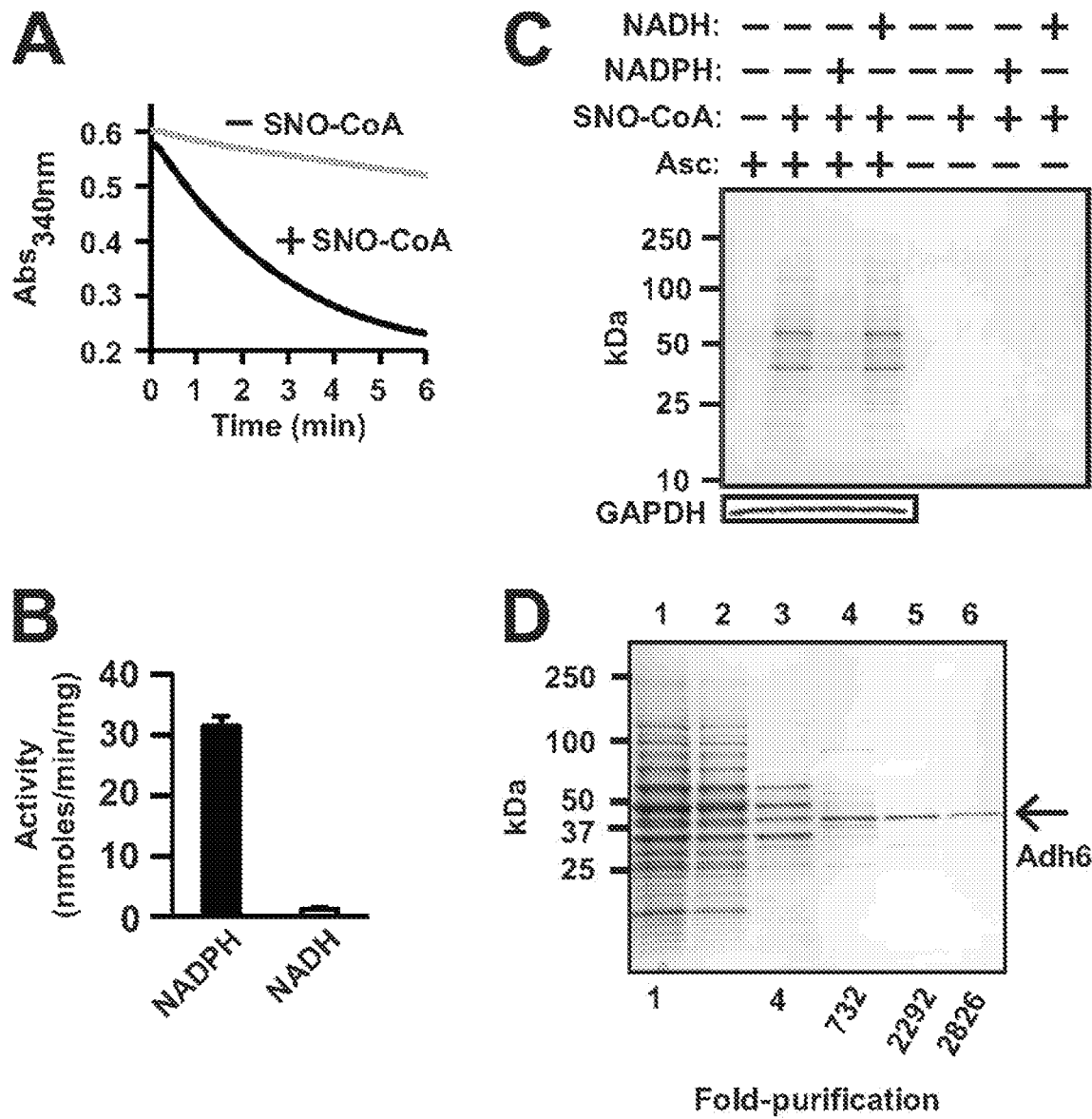
Figs. 1A-D

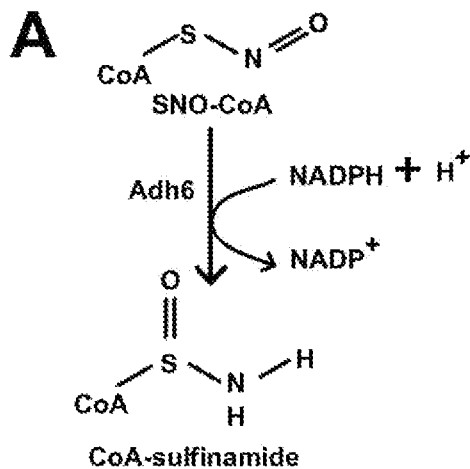
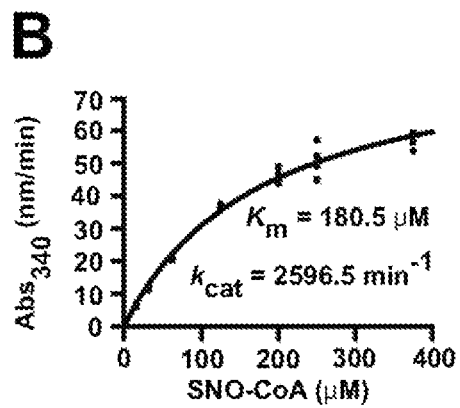
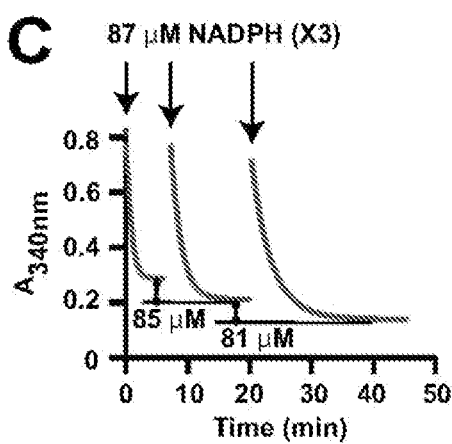
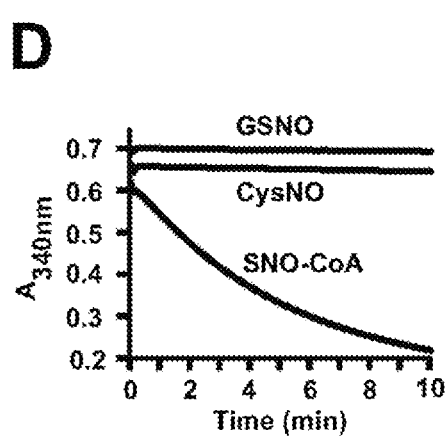
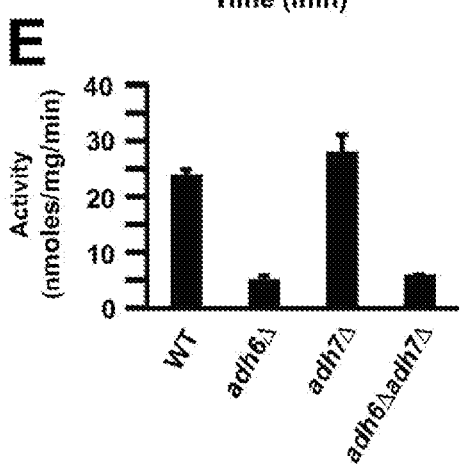
Figs. 2A-E

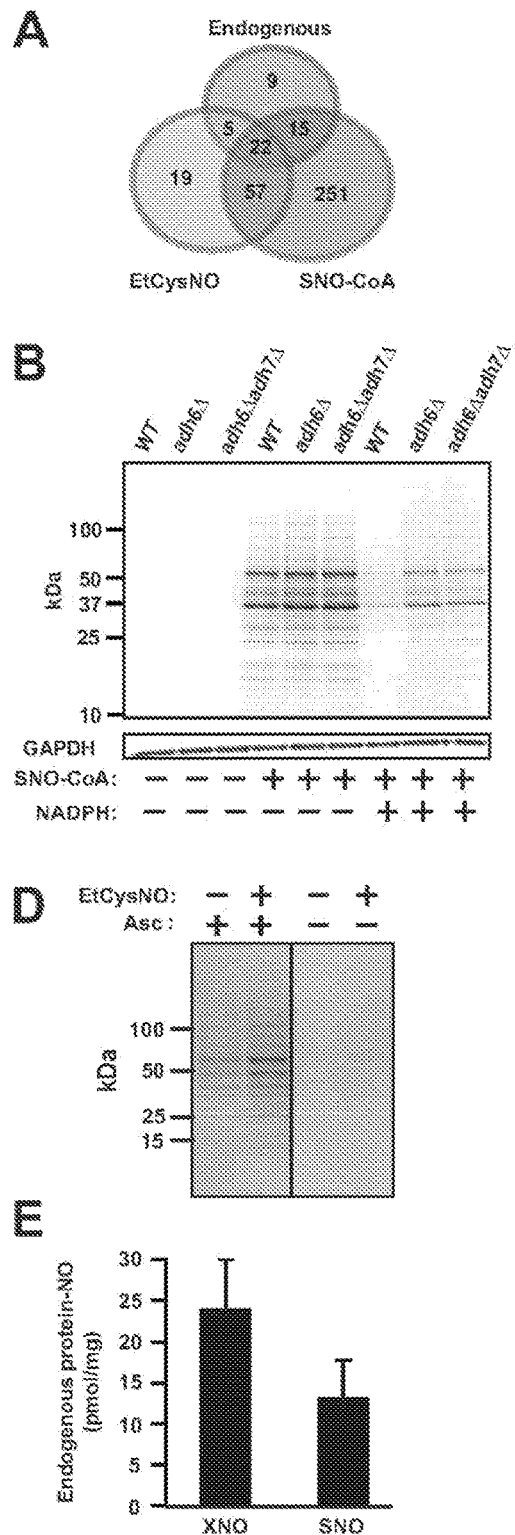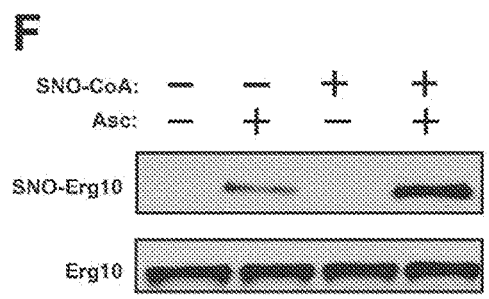
Figs. 3A-F

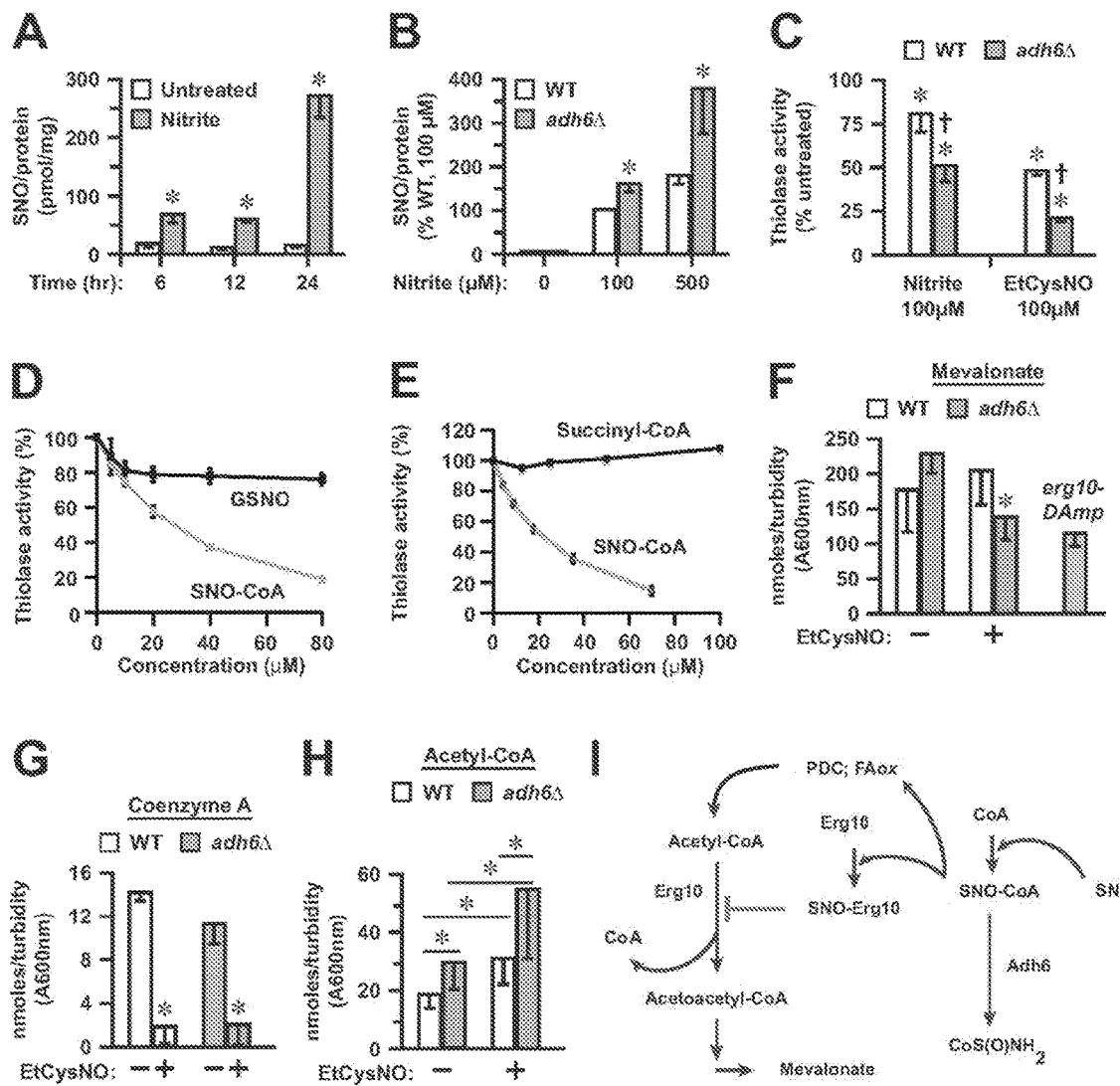
Figs. 4A-I

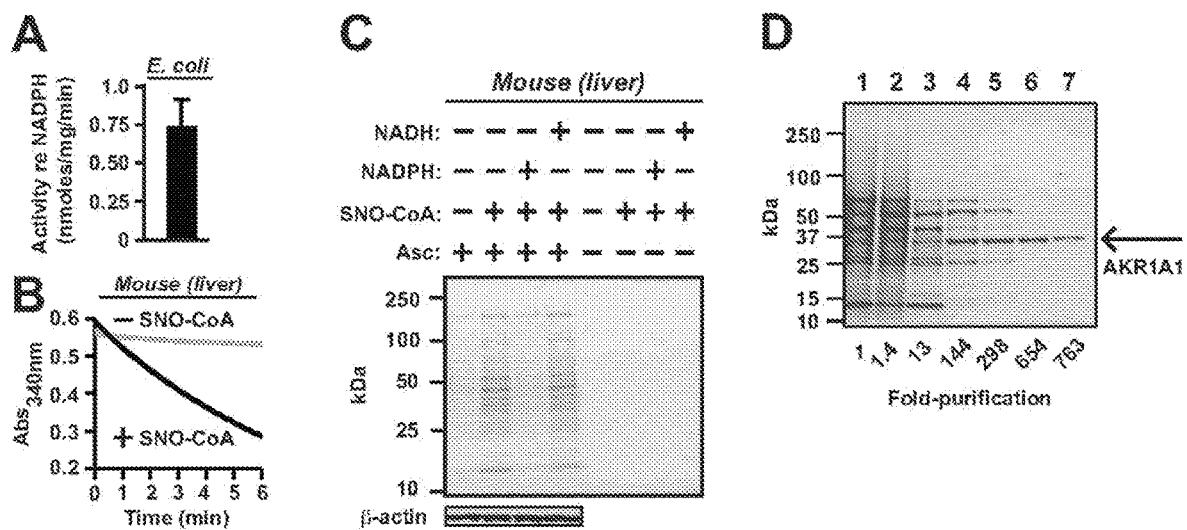
Fig. 5A-D
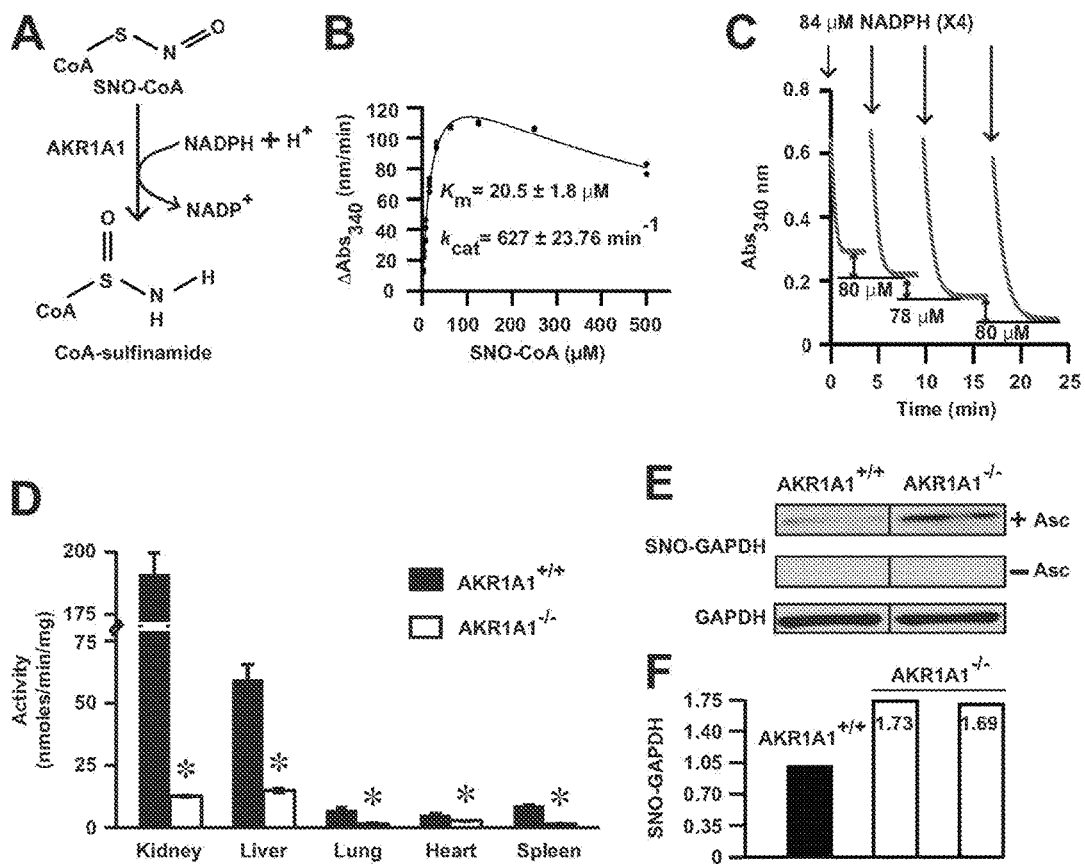
Figs. 6A-F

COMPOSITIONS AND METHODS OF MODULATING S-NITROSYLATION

RELATED APPLICATION

This application claims priority from U.S. Provisional Application No. 62/088,002, filed Dec. 5, 2014, the subject matter of which is incorporated herein by reference in its entirety.

TECHNICAL FIELD

This application relates to compositions and methods of modulating protein nitrosylation and particularly relates to the use of alcohol dehydrogenase inhibitors, aldoketo reductase inhibitors, and/or SNO-Coenzyme A reductases inhibitors to treat disorders associated with NO/SNO deficiency, as well as to the use of SNO-Coenzyme A as a nitrosylating agent.

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO capable of controlling biological events between adjacent cells and within cells, but present problems with the ability to regulate its activity.

As free radical gas, NO is reactive and unstable, thus NO is short lived in vivo, having a half life of 3-5 seconds or less under physiologic conditions. In the presence of oxygen or metals, NO can combine with thiols to generate a biologically important class of stable NO adducts called S-nitrosothiols (SNO's). This stable pool of NO has been postulated to act as a regulated source of bioactive NO and as such appears to be critically important in health and disease, given the centrality of NO in cellular homeostasis (Stamler et al., Proc. Natl. Acad. Sci. USA, 89:7674-7677 (1992)). Protein SNO's play broad roles in the function of cardiovascular, respiratory, metabolic, gastrointestinal, immune, and central nervous system (Foster et al., Trends in Molecular Medicine, 9 (4):160-168, (2003)). Low molecular weight SNOs provide NO bioactivity that is specific to the nature of the molecule. Heretofore the biology of low molecular weight SNOs was identified with S-nitrosoglutathione (GSNO). We now describe a novel class of nitrsoylating agent SNO-CoA.

Currently, there is a great need in the art for diagnostics, prophylaxis, ameliorations, and treatments for medical conditions relating to increased NO synthesis and/or increased NO bioactivity. There is need for regulating individual SNOs. In addition, there is a significant need for novel compounds, compositions, and methods for preventing, ameliorating, or reversing other SNO-associated disorders. The only available means to raise GSNO is through inhibition of known GSNO reductases, primarily ADH3 (glutathione dependent formaldehyde denhydrogenase) and carbonyl reductase.

SUMMARY

Embodiments described herein relate to compositions and methods of modulating protein nitrosylation and particularly relates to the use of alcohol dehydrogenase (ADH) inhibitors (e.g., ADH6 inhibitors), aldoketo reductase (AKR) inhibitors (e.g., AKR1A1 inhibitors), and/or SNO-Coenzyme A reductase (SNO-CoAR) inhibitors (e.g., ADH6 inhibitors and AKR1A1 inhibitors) to treat disorders associated with NO/SNO deficiency as well as to use the of SNO-Coenzyme A as a nitrosylating agent. ADH6 (yeast) and AKR1A1 (mammals) were found to reduce SNO-Coenzyme A (SNO-CoA), a newly discovered endogenous nitrosylating agent, and thus are responsible for denitrosylation of multiple novel proteins. AKR1A1 was also found to metabolize GSNO, a known nitrosylating agent. Inhibition of ADHs (e.g., ADH6), AKRs (e.g., AKR1A1), and/or SNO-CoAR (e.g., ADH6 and AKR1A1) can raise SNO levels and increase the S-nitrosylation of unique sets of proteins, which regulate cell metabolism. Administration of ADH inhibitors, AKR inhibitors, and/or SNO-CoAR inhibitors to a subject or microbe can raise SNO levels in the subject or microbe, promote protein S-nitrosylation, and treat disorders associated with NO/SNO deficiency. Moreover, administration of SNO-CoA to a subject or microbe can raise SNO levels in the subject or microbe, promote protein S-nitrosylation, and treat disorders associated with NO/SNO deficiency.

Multiple diseases and pathological conditions are associated with disruptions in protein S-nitrosylation. For example, it has been shown that storage of red blood cells (RBCs) leads to a rapid depletion of S-nitrosylated hemoglobin (SNO-Hb), a principal regulator of tissue oxygen delivery. In addition, heart disease, diabetes, Cystic Fibrosis, asthma, sickle cell disease, pulmonary hypertension, stroke, multiple sclerosis, and ischemia are among the many conditions characterized by diminished SNOs. Loss of SNO-Hb also impairs the ability of banked blood to dilate blood vessels after transfusion, resulting in exacerbation rather than correction of anemia-induced reduction in tissue oxygenation. Additionally, SNO CoA-metabolizing enzymes are identified as regulators of cholesterol metabolism and sterol biosynthesis.

Accordingly, in some embodiments ADH inhibitors, AKR inhibitors, and/or SNO-CoAR inhibitors can be administered to a subject to raise SNO levels and increase S-nitrosylation of proteins in the subject and treat disorders associated with NO/SNO deficiency or disruptions in protein S-nitrosylation, promote maintenance (or restoration) of SNO-Hb levels ("renitrosylation"), lower cholesterol levels, treat ischemia, and treat disorders associated with NO/SNO deficiency, such as cystic fibrosis, asthma, inflammatory bowel disease, hypertension, heart failure, acute coronary syndromes, impotence, stroke, septic shock, as well as promote liver regeneration, stem cell enhancement, antimicrobial activity, and protect against against ischemic injury, including renal ischemia and cardiac ischemia.

Other embodiments described herein relate to methods of treating a disorder ameliorated by NO donor therapy in a subject in need thereof. Such a method comprises administering a therapeutically effective amount of a pharmaceutical composition comprising at least one ADH inhibitor, AKR inhibitor, and/or SNO-CoAR inhibitor or a pharmaceutically acceptable salt, stereoisomer, prodrug, or metabolite thereof, in combination with at least one pharmaceutically acceptable carrier.

Still other embodiments described herein relate to methods of treating a disorder ameliorated by NO donor therapy in a subject in need thereof by administering a therapeutically effective amount of a pharmaceutical composition comprising SNO-CoA or a pharmaceutically acceptable salt, stereoisomer, prodrug, or metabolite thereof, in combination with at least one pharmaceutically acceptable carrier.

BRIEF DESCRIPTION OF THE DRAWINGS

FIGS. 1(A-D) illustrate the identification of alcohol dehydrogenase 6 (Adh6) as the NADPH-dependent SNO-CoA reductase in yeast. (A) SNO-CoA-dependent NADPH consumption in yeast (S. cerevisiae). Extracts (800 µg/ml) were incubated with 100 µM SNO-CoA and 100 µM NADPH, and NADPH consumption (absorbance at 340 nm) was monitored continuously. (B) SNO-CoA metabolizing activity in yeast extracts requires NADPH and not NADH. Extracts were incubated with 200 µM SNO-CoA and 100 µM NADPH or NADH and monitored continuously for 1 min. Data are presented as mean±SD; n=3. (C) SNO-CoA mediated protein S-nitrosylation. Representative Coomassie-stained SDS-PAGE gel displaying SNO-proteins isolated by SNO-RAC following incubation of yeast lysate for 10 min with SNO-CoA (60 µM) alone or in combination with NADPH or NADH (100 µM). Ascorbate (Asc) was omitted from the SNO-RAC assay as a specificity control. Results are representative of 3 independent experiments. (D) Isolation and identification of SNO-CoA reductase. Representative Coomassie-stained SDS-PAGE gel corresponding to the five-step chromatographic purification scheme detailed in Table 1, which yielded from a crude extract (lane 1) 2826-fold enrichment of NADPH-dependent SNO-CoA reductase activity identified by mass spectrometry as Adh6 (lane 6).

FIGS. 2(A-E) illustrate the characterization of the yeast SNO-CoA reductase, Adh6. (A) CoA-sulfinamide was identified by mass spectrometry as the major stable product of SNO-CoA reduction by purified Adh6 (see FIGS. 7C, D and F for product analysis). (B) Kinetic analysis of SNO-CoA reductase activity of purified Adh6. (C) Stoichiometry of NADPH:SNO-CoA in Adh6-catalyzed SNO-CoA reduction. Sequential additions of 87 µM NADPH to an excess of SNO-CoA led to consumption of 79-85 µM (mean 82±3 µM; n=6 additions) of SNO-CoA, demonstrating a stoichiometry of 1:1. Results are representative of two independent experiments. (D) Specificity of Adh6 for SNO-CoA. Purified Adh6 (FIG. 1D) (20 nM) was incubated with NADPH (100 µM) and SNO-CoA, GSNO or CysNO (100 µM) and NADPH consumption was measured over time. (E) Adh6 is the principal source of NADPH-dependent SNO-CoA reductase activity. Activity was assayed in lysates from WT yeast and adh6Δ, adh7Δ and adh6Δadh7Δ yeast. Data are presented as mean±SD; n=3.

FIGS. 3(A-F) illustrate Adh6 regulates protein S-nitrosylation mediated by SNO-CoA. (A) A Venn diagram illustrates the relationships between the sets of SNO-proteins identified in intact WT yeast under basal growth conditions (endogenous SNO-proteins) or following treatment with EtCysNO, a cell-permeable S-nitrosylating agent, and in lysates treated with SNO-CoA. (B) Adh6-regulated protein S-nitosylation. Representative Coomassie-stained SDS-PAGE gel illustrating SNO-proteins isolated by SNO-RAC following treatment of WT yeast lysates with SNO-CoA (in the presence or absence of NADPH) and the regulation by Adh6 of protein S-nitrosylation. Results are representative of 3 independent experiments. (C) SNO-CoA mediated protein S-nitrosylation in situ. (Top) SNO-proteins exhibiting enhanced S-nitrosylation in adh6Δ versus WT yeast following treatment with EtCysNO. (Bottom) Endogenous SNO-proteins showing enhanced S-nitrosylation in adh6Δ versus WT yeast under basal growth conditions. Shared targets identified following treatment of lysates with SNO-CoA are indicated in red and metabolic enzymes are underlined. N=3; p<0.05 by Student's t-test; RSD<35%. (D) Isolation of endogenous and in-situ formed SNO-proteins. Representative Coomassie-stained SDS-PAGE gel illustrating endogenous SNO-proteins isolated by SNO-RAC from WT yeast (untreated) as well as SNO-proteins formed in situ (EtCysNO). Shared targets are shown in (A). (Note that the demonstration of endogenous SNO-proteins in (D) but not (B) reflects different amounts of total protein employed in the SNO-RAC assay (4 versus 1 mg, respectively). Results are representative of 3 independent experiments. (E) Endogenous protein-bound NO. Total protein-bound NO (XNO, which includes FeNO and SNO) and SNO were quantified in WT yeast extracts by mercury-coupled photolysis-chemiluminescence. Data are presented as mean±SEM (n=7). (F) Endogenous S-nitrosylation of thiolase and its enhanced S-nitrosylation by SNO-CoA. Results of a representative analysis by SNO-RAC of endogenous and SNO-CoA-induced S-nitrosylation of Erg10. Data are representative of 2 independent experiments.

FIGS. 4(A-I) illustrate S-nitrosylation by SNO-CoA inhibits acetoacetyl-CoA thiolase (Erg10)-dependent metabolism. (A) Endogenous SNO-protein formation in yeast grown under hypoxia in the presence of nitrite. WT yeast were grown for the indicated times in the presence or absence of 100 µM nitrite. SNO levels in lysates were quantified by mercury-coupled photolysis chemiluminescence. Data are presented as mean±SEM (n=4; *, p<0.05 by Student's t-test). (B) Adh6 regulates endogenous SNO-protein synthesis in yeast. Cells were grown under hypoxia for 24 hr in the presence of 0, 100 or 500 µM nitrite and SNO-protein levels in lysates were quantified as in (A). Data are presented as mean±SEM (n=5; *, p<0.05 by Student's t-test). (C) Erg10 activity is inhibited by Adh6-regulated, SNO-CoA-mediated S-nitrosylation. Erg10 activity was assayed in extracts of WT or adh6Δ yeast grown under hypoxia with or without 100 µM nitrite (as in A, B), or treated at normoxia with EtCysNO (100 µM). Data are mean±SD (n=3; *, p<0.05 versus untreated and †, p<0.05 adh6Δ, versus WT by ANOVA. (D, E) Selective inhibition of Erg10 by SNO-CoA versus GSNO (D) or succinyl-CoA (E). Erg10 activity was assayed in extracts of WT yeast in the presence or absence of SNO-CoA (D, E), GSNO (D) or succinyl-CoA (E). (F, G, H). Effects of enhanced S-nitrosylation on the metabolic profile of the mevalonate pathway. Mid-log phase yeast were untreated or treated with 100 µM (F) or 500 µM (G, H) EtCysNO for 2 hr and metabolites (mevalonate, CoA and acetyl-CoA) were measured as described in Supplementary Materials and Methods. Data are mean±SD (n=5-6; *, p<0.05 by Student's t-test in (F) and (G) and by ANOVA in (H), normalized with respect to culture turbidity). Note in (F) that erg10-DAmP yeast exhibit ~50% of wild-type thiolase activity. (I) Schematic summary of the potential role of SNO-CoA-mediated protein S-nitrosylation in regulation of Erg10-dependent metabolism. Erg10 converts acetyl-CoA to free CoA and acetoacetyl-CoA, a precursor via HMG-CoA in mevalonate biosynthesis. S-nitrosylation of Erg10 by SNO-CoA, regulated by Adh6 acting as a SNO-CoA reductase, inhibits thiolase activity resulting in decreased levels of mevalonate and may contribute to diminished levels of CoA and increased levels of acetyl-CoA. Altered levels of CoA and acetyl-CoA may reflect actions of Adh6-regulated SNO-CoA at additional loci (FAox, fatty acid β-oxidation; PDC, pyruvate dehydrogenase multi-enzyme complex). SNO-CoA reductase thus acts as a cognate denitrosylase for substrates of SNO-CoA, by direct analogy to GSNO reductase, which acts as a denitrosylase for protein substrates of GSNO.

FIGS. 5(A-D) illustrate the identification of aldo-keto reductase 1A1 (AKR1A1) as the NADPH-dependent SNO-CoA reductase in mammals. A and B, Conservation of SNO-CoA reductase activity from bacteria to mammals. NADPH-dependent SNO-CoA metabolizing activity in extracts from E. coli (A) and mouse liver (B). Conditions in (A) similar to FIG. 1B; in (B), 160 µg/ml of liver extract was incubated with 100 µM SNO-CoA and 100 µM NADPH. Note that high levels of basal NADH consumption (diaphorase activity) in E. coli under aerobic conditions prevented assessment of SNO-CoA dependence. (C) SNO-CoA mediated protein S-nitrosylation. Representative Coomassie-stained SDS-PAGE gels displaying SNO-proteins isolated by SNO-RAC following incubation of mouse liver extract (1 mg/ml in 1 ml reaction volume) for 10 min with SNO-CoA (60 µM) alone or in combination with NADPH or NADH (100 µM). Ascorbate (Asc) was omitted from the SNO-RAC assay as a specificity control. (D) SNO-CoA reductase isolation. Representative Coomassie-stained SDS-PAGE gel corresponding to the six-step chromatographic purification scheme, which yielded from a crude extract (lane 1) 763-fold enrichment of NADPH-dependent SNO-CoA reductase activity identified by mass spectrometry as AKR1A1 (lane 7).

FIGS. 6(A-F) illustrate the characterization of the mammalian SNO-CoA reductase, AKR1A1. (A) CoA-sulfinamide was identified by mass spectrometry as the major stable product of SNO-CoA reduction by purified AKR1A1. (B) Kinetic analysis of SNO-CoA reductase activity of purified AKR1A1. (C) Stoichiometry of NADPH:SNO-CoA in AKR1A1-catalyzed SNO-CoA reduction. Sequential additions of 84 µM NADPH to an excess of SNO-CoA led to consumption of 75-82 µM (mean 79±3 µM; n=8 additions) of SNO-CoA, demonstrating a stoichiometry of 1:1. Results shown are representative of two independent experiments. (D) SNO-CoA reductase activity in AKR1A1 knockout animals. NADPH-dependent SNO-CoA reductase activity across various tissues from wild-type or AKR1A1$^{-/-}$ mice. Extracts were incubated with 100 µM NADPH and 0 or 200 µM SNO-CoA. Values are from 3 wild-type (filled) and 3 AKR1A1$^{-/-}$ (open) mice. *, p<0.05 by Student's t-test. (E and F) Regulation of endogenous protein S-nitrosylation by AKR1A1. Analysis of S-nitrosylated GAPDH (SNO-GAPDH) in kidney extracts of AKR1A1$^{+/+}$ and AKR1A1$^{-/-}$ mice. Changes in SNO-GAPDH levels were determined by SNO-RAC coupled to (E) Western Blotting (n=2) or to (F) iTRAQ-based mass spectrometry (n=2).

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g. sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, $3^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)—O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—O), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)(OH)$_2$), phosphonato (—P(O)(O$^-$)$_2$), phosphinato (—P(O)(O$^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to compositions and methods of modulating protein nitrosylation and particularly relates to the use of alcohol dehydrogenase (ADH) inhibitors (e.g., ADH6 inhibitors), aldoketo reductase (AKR) inhibitors (e.g., AKR1A1 inhibitors), and/or SNO-Coenzyme A reductase (SNO-CoAR) inhibitors (e.g., ADH6 inhibitors and AKR1A1 inhibitors) to treat disorders associated with NO/SNO deficiency as well as to use the of SNO-Coenzyme A as a nitrosylating agent. ADH6 (yeast) and AKR1A1 (mammals) were found to reduce SNO-Coenzyme A (SNO-CoA), a newly discovered endogenous nitrosylating agent, and thus are responsible for denitrosylation of multiple novel proteins. AKRA1A1 was also found to metabolize GSNO, a known nitrosylating agent. Inhibition of ADHs (e.g., ADH6), AKRs (e.g., AKR1A1), and/or SNO-CoAR (e.g., ADH6 and AKR1A1) can raise SNO levels and increase the S-nitrosylation of unique sets of proteins, which regulate cell metabolism. Administration of ADH inhibitors, AKR inhibitors, and/or SNO-CoAR inhibitors to a subject or microbe can raise SNO levels in the subject or microbe, promote protein S-nitrosylation, and treat disorders associated with NO/SNO deficiency or can be employed to raise levels therapeutically. Moreover, administration of SNO-CoA to a subject or microbe can raise SNO levels in the subject or microbe, promote protein S-nitrosylation, and treat disorders associated with NO/SNO deficiency.

Administration of ADH inhibitors, AKR inhibitors, and/or SNO-CoAR inhibitors as well as SNO-CoA (or derivatives thereof e.g. SNO-cysteamine) to a subject in need thereof can raise SNO levels in the subject and treat disorders associated with unique NO/SNO deficiency or disruptions in protein S-nitrosylation, promote maintenance (or restoration) of SNO-Hb levels ("renitrosylation"), lower cholesterol levels, treat ischemia, and treat disorders associated with NO/SNO deficiency, such as cystic fibrosis, asthma, inflammatory bowel disease, stroke, cardiovascular disease, acute coronary syndromes, impotence, septic shock, as well as promote liver regeneration, stem cell enhancement, and antimicrobial activity.

In some embodiments, the AKR inhibitor can be a selective AKR1A1 inhibitor or a partially selective AKR1A1 that can inhibit other aldo-keto reductase family members, such as AKR1B1. In some embodiments, the AKR1A1 inhibitor can have an $IC_{50} \leq 100$ nM. In other embodiments, the AKR1A1 inhibitor can have a selectivity for AKR1A1 versus AKR1B1$\geq$10 times. In other embodiments, the AKR1A1 inhibitor can have a selectivity for AKR1A1 versus other AKRs$\geq$50 times. In still other embodiments, the AKR1A1 inhibitor can have an AKR1A1 $IC_{50} \leq 25$ nM and an AKR1B1/AKR1A1 $IC_{50} \leq 300$ nM (e.g., less than 100 nM).

Examples of selective and partially selective AKR1A1 inhibitors can include Imirestat (2,7-Difluoro-2'H,5'H-spiro[fluorene-9,4'-imidazolidine]-2',5'-dione) and analogues thereof.

In some embodiments, the imirestat analogues can include compounds selected from the group consisting of:

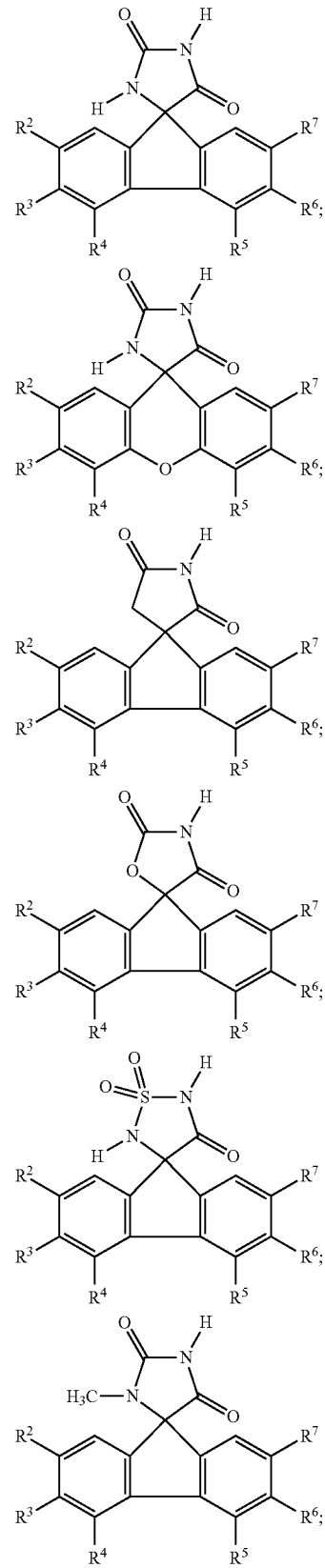

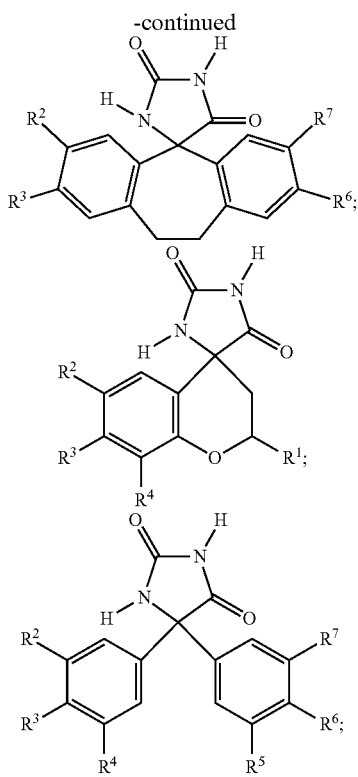

each $R^1$, $R^2$, $R^3$, $R^4$, $R^5$, $R^6$, and $R^7$ are the same or different and are one or more substituent selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO), carbamoyl (—(CO)—NH$_2$), $C_1$-$C_{24}$ alkyl-carbamoyl (—(CO)—NH($C_1$-$C_{24}$ alkyl)), arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—O—N$^+$=C$^-$), isothiocyanato (—S—CN), azido (—N=N$^+$=N$^-$), formyl (—(CO)—H), thioformyl (—(CS)—H), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO2NR2 where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide (—SO$_2$—NH2, —SO$_2$NY$_2$ (wherein Y is independently H, arlyl or alkyl), phosphono (—P(O)(OH)$_2$), phosphonato (—P(O)(O$^-$)$_2$), phosphinato (—P(O)(O)), phospho (—PO$_2$), phosphino (—PH$_2$), polyalkyl ethers (—[(CH$_2$)$_n$O]$_m$), phosphates, phosphate esters [—OP(O)(OR)$_2$ where R=H, methyl or other alkyl], groups incorporating amino acids or other moieties expected to bear positive or negative charge at physiological pH, and combinations thereof; and pharmaceutically acceptable salts thereof.

Other examples of selective and partially selective AKR1A1 inhibitors can include Methyl[4-oxo-2-(substituted benzoylimino)-3-(substituted phenyl)thiazolidin-5-ylidene]acetate derivatives recited in S. Ali et al., "Design, synthesis and molecular modeling of novel methyl[4-oxo-2-(aroylimino)-3-(substituted phenyl)thiazolidin-5-ylidene] acetates as potent and selective aldose reductase inhibitors", Med. Chem. Commun., 2012, 3, 1428-1434. These AKR1A1 inhibitors can have the following formula:

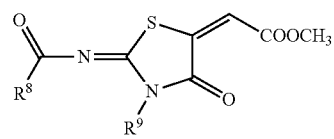

wherein $R^8$ and $R^9$ are independently selected from the group consisting of substituted and unsubstituted aryls.

Other examples of selective and partially selective AKR1A1 inhibitors can include benzothiazolyl substituted iminothiazolidinones and benzamido-oxothiazolidines recited in Saeed et al., "Benzothiazolyl substituted iminothiazolidinones and benzamido-oxothiazolidines as potent and partly selective aldose reductase inhibitors", Med. Chem. Commun., 2014, 5, 1371-1380. These AKR1A1 inhibitors can have the following formula:

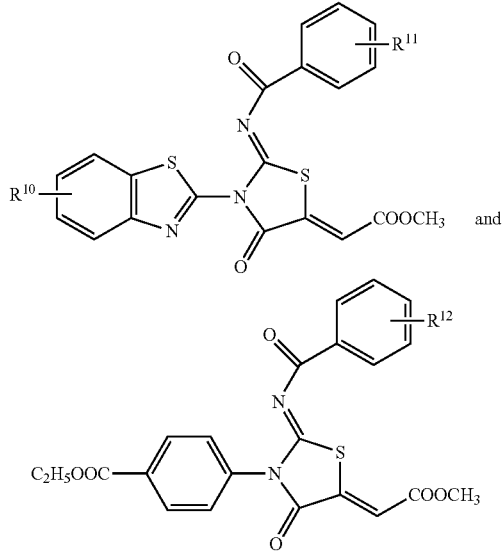

and wherein $R^{10}$, $R^{11}$, or $R^{12}$ include one or more substituent and are each independently selected from the group consisting of H, a halogen (e.g., 6-Br, 3-Cl, 2-F, 2-Br, 5,6-di-Cl, 2,4-di-Cl), lower alkyl, and methoxy (e.g., 4-OCH$_3$, 3,4-OCH$_3$).

Still other examples of selective and partially selective AKR1A1 inhibitor are disclosed in the following publications: Mechanism of Human Aldehyde Reductase: Characterization of the Active Site Pocket, Oleg A. Barski et al., Biochemistry 1995, 34, 11264-11275, In vivo role of aldehyde reductase, M. Takahashi et al., Biochim Biophys Acta. 2012 November; 1820(11):1787-96, The Aldo-Keto Reductase Superfamily and its Role in Drug Metabolism and Detoxification, Oleg A. Barski et al., Drug Metab Rev. 2008; 40(4): 553-624, Asborin Inhibits Aldo/Keto Reductase 1A1, Matthias Scholz et al., Chem Med Chem, 2011, 6, 89-93, Inhibition of Aldehyde Reductase by Aldose Reductase Inhibitors, Sanai Sato et al., Biochemical Pharmacology, 1990. 40, 1033-1042, Inhibition of human aldose and aldehyde reductases by non-steroidal anti-inflammatory drugs, D. Michelle Ratliff et al., Advances in Experimental Medicine and Biology, Volume: 463, Issue: Enzymology and Molecular Biology of Carbonyl Metabolism 7, Pages: 493-499 (1999), Inhibition of aldehyde reductases, Philip J Schofield et al., Progress in Clinical and Biological Research, 1987, 232, Issue: Enzymol. Mol. Biol. Carbonyl Metab., 287-96, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, all of which are incorporated herein by reference in their entirety. It will be appreciated that any potential selective or partially selective AKR1A1 inhibitors can be used in the compositions and methods recited herein.

The ADH inhibitor can be include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, O-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2,2-trichloroethanol, 4,5-diaminopyrazole and its derivatives and 2-ethyl-5-methyl-2H-3,4-diaminopyrazole. See U.S. Patent Application Publication 20030138390, which is incorporated herein by reference in its entirety.

Fomepizole (4-methylpyrazole) is also a competitive inhibitor of ADH. Pyrazole and its 4-substituted derivatives competitively inhibit the binding of alcohol substrates through the formation of a tight enzyme.NAD$^+$.inhibitor complex, in which pyrazole nitrogens interact with both zinc and NAD$^+$. Xie et al., J. Biol. Chem., 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., J. Med. Chem., 37:392-9 (1994), herein incorporated by reference.

Other ADH inhibitors include dimethyl sulfoxide, Perlman and Wolff, Science, 160:317-9 (1968); and p-methylbenzyl hydroperoxide, Skursky et al., Biochem Int., 26:899-904 (1992), herein incorporated by reference.

In some embodiments, the ADH inhibitor can be a selective ADH6 inhibitor or partially selective ADH6 inhibitor that does not inhibit ADH3. In other embodiments, the ADH inhibitor does not inhibit ADH3 but inhibits other ADHs, such as ADH6.

In other embodiments, the ADH inhibitor and/or AKR inhibitor can include an agent that reduces or inhibits ADH and/or AKR expression, such as ADH6 expression or AKR1A1 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the ADH and/or AKR expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res,* 25:776-780; *J Mol Recog* 7:89-98; *Nucleic Acids Res* 23:2661-2668; *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA,* 98:9742-9747; *EMBO J,* 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev,* 2002, 16:948-58; *Nature,* 2002, 418:38-9; *RNA,* 2002, 8:842-50; and *Proc Natl Acad Sci,* 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the AKR1A1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E. coli* strain DH5α cells. After positive clones are selected, plasmid can be transfected into 293T cells by calcium precipitation. The viral supernatant collected containing shRNA can then be used to infect mammalian cells in order to down regulate the AKR1A1.

AKR1A1 siRNA, shRNA plasmids, and shRNA lentiviral particle gene silencers are commercially available from Santa Cruz Biotechnology under the product names sc-78566, sc-78566-SH, and sc-78566-V.

In another embodiment, the ADH and/or AKR inhibitor can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., AKR1A1).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

The ADH inhibitors, AKR inhibitors, and/or SNO-CoAR inhibitors can be provided in pharmaceutical compositions with at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The compositions comprising ADH inhibitors, AKR inhibitors, and/or SNO-CoAR inhibitors can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the ADH inhibitors, AKR inhibitors, and/or SNO-CoAR inhibitors can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

For respiratory disorders, an inhalation formulation can be used to achieve high local concentrations. Formulations suitable for inhalation include dry power or aerosolized or vaporized solutions, dispersions, or suspensions capable of being dispensed by an inhaler or nebulizer into the endobronchial or nasal cavity of infected patients to treat upper and lower respiratory bacterial infections.

Solutions or suspensions used for parenteral, intradermal, or subcutaneous application can comprise one or more of the following components: (1) a sterile diluent such as water for injection, saline solution, fixed oils, polyethylene glycols, glycerine, propylene glycol, or other synthetic solvents; (2) antibacterial agents such as benzyl alcohol or methyl parabens; (3) antioxidants such as ascorbic acid or sodium bisulfite; (4) chelating agents such as ethylenediaminetetraacetic acid; (5) buffers such as acetates, citrates, or phosphates; and (5) agents for the adjustment of tonicity such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the ADH inhibitors, AKR inhibitors, and/or SNO-CoAR inhibitors are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

Pharmaceutical compositions that include the ADH inhibitors, AKR inhibitors, and/or SNO-CoAR inhibitors can comprise one or more pharmaceutical excipients. Examples of such excipients include, but are not limited to binding agents, filling agents, lubricating agents, suspending agents, sweeteners, flavoring agents, preservatives, buffers, wetting agents, disintegrants, effervescent agents, and other excipients. Such excipients are known in the art. Exemplary excipients include: (1) binding agents which include various celluloses and cross-linked polyvinylpyrrolidone, microcrystalline cellulose, silicified microcrystalline cellulose, gum tragacanth and gelatin; (2) filling agents such as various starches, lactose, lactose monohydrate, and lactose anhydrous; (3) disintegrating agents such as alginic acid, Primogel, corn starch, lightly crosslinked polyvinyl pyrrolidone, potato starch, maize starch, and modified starches, croscarmellose sodium, cross-povidone, sodium starch glycolate, and mixtures thereof; (4) lubricants, including agents that act on the flowability of a powder to be compressed, include magnesium stearate, colloidal silicon dioxide, talc, stearic acid, calcium stearate, and silica gel; (5) glidants such as colloidal silicon dioxide; (6) preservatives, such as potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride; (7) diluents such as pharmaceutically acceptable inert fillers, such as microcrystalline cellulose, lactose, dibasic calcium phosphate, saccharides, and/or mixtures of any of the foregoing; examples of diluents include microcrystalline cellulose; lactose such as lactose monohydrate, and lactose anhydrous; dibasic calcium phosphate, mannitol; starch; sorbitol; sucrose; and glucose; (8) sweetening agents, including any natural or artificial sweetener, such as sucrose, saccharin sucrose, xylitol, sodium saccharin, cyclamate, aspartame, and acesulfame; (9) flavoring agents, such as peppermint, methyl salicylate, orange flavoring, bubble gum flavor, fruit flavors, and the like; and (10) effervescent agents, including effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

In some embodiments, the ADH inhibitors, AKR inhibitors, and/or SNO-CoAR inhibitors including pharmaceutical compositions comprising the ADH inhibitors, AKR inhibitors, and/or SNO-CoAR inhibitors can be used in methods for preventing or treating (e.g., alleviating one or more symptoms of) medical conditions. The methods comprise administering a therapeutically effective amount of the ADH inhibitors, AKR inhibitors, and/or SNO-CoAR inhibitors to a patient or subject in need thereof. The compositions can also be used for prophylactic therapy.

The patient can be any animal, domestic, livestock, or wild, including, but not limited to cats, dogs, horses, pigs, and cattle, and preferably human patients. As used herein, the terms patient and subject may be used interchangeably.

In general, the dosage, i.e., the therapeutically effective amount, ranges from 1 µg/kg to 10 g/kg and often ranges from 10 µg/kg to 1 g/kg or 10 µg/kg to 100 mg/kg body weight of the subject being treated, per day.

In some embodiments, the ADH inhibitors, AKR inhibitors, and/or SNO-CoAR inhibitors including pharmaceutical compositions comprising the ADH inhibitors, AKR inhibitors, and/or SNO-CoAR inhibitors can be used in a method of treating a subject afflicted with a disorder ameliorated by NO donor therapy. Such a method comprises administering to a subject a therapeutically effective amount of the ADH inhibitors, AKR inhibitors, and/or SNO-CoAR inhibitors.

The disorders can include pulmonary disorders associated with hypoxemia and/or smooth muscle constriction in the lungs and airways and/or lung infection and/or lung inflammation and/or lung injury (e.g., pulmonary hypertension, ARDS, asthma, pneumonia, pulmonary fibrosis/interstitial lung diseases, cystic fibrosis, COPD); cardiovascular disease and heart disease (e.g., hypertension, ischemic coronary syndromes, atherosclerosis, heart failure, glaucoma); diseases characterized by angiogenesis (e.g., coronary artery disease); disorders where there is risk of thrombosis occurring; disorders where there is risk of restenosis occurring; inflammatory diseases (e.g., AIDS related dementia, inflammatory bowel disease (IBD), Crohn's disease, colitis, and psoriasis); functional bowel disorders (e.g., irritable bowel syndrome (IBS)); diseases where there is risk of apoptosis occurring (e.g., heart failure, atherosclerosis, degenerative neurologic disorders, arthritis, and liver injury (ischemic or alcoholic)); impotence; sleep apnea; diabetic wound healing; cutaneous infections; treatment of psoriasis; obesity caused by eating in response to craving for food; stroke; reperfusion injury (e.g., traumatic muscle injury in heart or lung or crush injury); and disorders where preconditioning of heart or brain for NO protection against subsequent ischemic events is beneficial, central nervous system (CNS) disorders (e.g., anxiety, depression, psychosis, and schizophrenia); and infections caused by bacteria (e.g., tuberculosis, C. difficile infections, among others).

In other embodiments, the ADH inhibitors, AKR inhibitors, and/or SNO-CoAR inhibitors can be used to treat a subject that exhibits at least one symptom of an ischemic tissue or tissue damaged by ischemia. In particular embodiments, the subject is a human who is has or who is at risk of having an ischemic tissue or tissue damaged by ischemia, e.g., a subject that has diabetes, peripheral vascular disease, thromboangiitis obliterans, vasculitis, cardiovascular disease, coronary artery disease or heart failure, or cerebrovascular disease, cardiovascular disease, or cerebrovascular disease.

Illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia, and thus, suitable for treatment or amelioration using the methods described herein, include, but are not limited to, acute coronary syndrome, acute lung injury (ALI), acute myocardial infarction (AMI), acute respiratory distress syndrome (ARDS), arterial occlusive disease, arteriosclerosis, articular cartilage defect, aseptic systemic inflammation, atherosclerotic cardiovascular disease, autoimmune disease, bone fracture, bone fracture, brain edema, brain hypoperfusion, Buerger's disease, burns, cancer, cardiovascular disease, cartilage damage, cerebral infarct, cerebral ischemia, cerebral stroke, cerebrovascular disease, chemotherapy-induced neuropathy, chronic infection, chronic mesenteric ischemia, claudication, congestive heart failure, connective tissue damage, contusion, coronary artery disease (CAD), critical limb ischemia (CLI), Crohn's disease, deep vein thrombosis, deep wound, delayed ulcer healing, delayed wound-healing, diabetes (type I and type II), diabetic neuropathy, diabetes induced ischemia, disseminated intravascular coagulation (DIC), embolic brain ischemia, graft-versus-host disease, frostbite, hereditary hemorrhagic telengiectasiaischemic vascular disease, hyperoxic injury, hypoxia, inflammation, inflammatory bowel disease, inflammatory disease, injured tendons, intermittent claudication, intestinal ischemia, ischemia, ischemic brain disease, ischemic heart disease, ischemic peripheral vascular disease, ischemic placenta, ischemic renal disease, ischemic vascular disease, ischemic-reperfusion injury, laceration, left main coronary artery disease, limb ischemia, lower extremity ischemia, myocardial infarction, myocardial ischemia, organ ischemia, osteoarthritis, osteoporosis, osteosarcoma, Parkinson's disease, peripheral arterial disease (PAD), peripheral artery disease, peripheral ischemia, peripheral neuropathy, peripheral vascular disease, pre-cancer, pulmonary edema, pulmonary embolism, remodeling disorder, renal ischemia, retinal ischemia, retinopathy, sepsis, skin ulcers, solid organ transplantation, spinal cord injury, stroke, subchondral-bone cyst, thrombosis, thrombotic brain ischemia, tissue ischemia, transient ischemic attack (TIA), traumatic brain injury, ulcerative colitis, vascular disease of the kidney, vascular inflammatory conditions, von Hippel-Lindau syndrome, and wounds to tissues or organs.

Other illustrative examples of genetic disorders, syndromic conditions, traumatic injuries, chronic conditions, medical interventions, or other conditions that cause or are associated with ischemia, or increase the risk of ischemia in a subject, or cause a subject to exhibit more or more symptoms of ischemia suitable for treatment or amelioration using the methods of the present invention, include, ischemia resulting from surgery, chemotherapy, radiation therapy, or cell, tissue, or organ transplant or graft.

In various embodiments, the methods can be used for treating cerebrovascular ischemia, myocardial ischemia, limb ischemia (CLI), myocardial ischemia (especially chronic myocardial ischemia), ischemic cardiomyopathy, cerebrovascular ischemia, renal ischemia, pulmonary ischemia, intestinal ischemia, and the like.

In various embodiments, pharmaceutical compositions described herein can be used to treat an ischemic tissue in which it is desirable to increase the blood flow, oxygen supply, glucose supply, or supply of nutrients to the tissue.

In one embodiment, the ADH inhibitors, AKR inhibitors, and/or SNO-CoAR inhibitors or a pharmaceutically acceptable salt thereof, or a prodrug or metabolite thereof, can be administered in combination with an NO donor, including SNO-CoA, which is shown to have novel activity in regulating sterol biosynthesis and CoA metabolism. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy(N-nitrosamine), and perfluorocarbons that have been saturated with NO or a hydrophobic NO donor. ADH inhibitors, AKR inhibitors, and/or SNO-CoAR inhibitors can also be combined with with R(+) enantiomer of amlodipine, a known NO releaser (Zhang at al., J. Cardiovasc. Pharm. 39: 208-214 (2002)).

In some embodiments, the ADH inhibitors, AKR inhibitors, and/or SNO-CoAR inhibitors can be administered in a combinatorial therapy or combination therapy that includes administration of the ADH inhibitors, AKR inhibitors, and/or SNO-CoAR inhibitors with one or more additional active agents. The phrase "combinatorial therapy" or "combination therapy" embraces the administration of the ADH inhibitors, AKR inhibitors, and/or SNO-CoAR inhibitors, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the ADH inhibitors, AKR inhibitors, and/or SNO-CoAR inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5α-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11): 1465-1473).

Other active compounds, which can be present in pharmaceutical and/or cosmetic compositions can include aminexil and its derivatives, 60-[(9Z,12Z)octadec-9,12-dienoyl] hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium panthotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexasaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

It will also be appreciated that certain selective ADH inhibitors, AKR inhibitors, and/or SNO-CoAR inhibitors that inhibit some ADHs, AKRs, and/or SNO-CoARs can be administered in combination with other selective ADH inhibitors, AKR inhibitors, and/or SNO-CoAR inhibitors that inhibit other ADHs, AKRs, and/or SNO-CoARs. For example, a selective ADH6 inhibitor can be administered in combination with an ADH3 inhibitor.

Still other embodiments described herein relate to a method of treating a subject afflicted with pathologically proliferating cells where the method comprises administering to said subject a therapeutically effective amount of the ADH inhibitors, AKR inhibitors, and/or SNO-CoAR inhibitors.

The pathologically proliferating cells can be pathologically proliferating microbes. The microbes involved can be those where an ADH, such as GSNOR, is expressed to protect the microbe from nitrosative stress or where a host cell infected with the microbe expresses the enzyme, thereby protecting the microbe from nitrosative stress. The term "pathologically proliferating microbes" is used herein to mean pathologic microorganisms including, but not limited to, pathologic bacteria, pathologic viruses, pathologic *Chlamydia*, pathologic protozoa, pathologic *Rickettsia*, pathologic fungi, and pathologic mycoplasmata. More detail on the applicable microbes is set forth at columns 11 and 12 of U.S. Pat. No. 6,057,367. The term "host cells infected with pathologic microbes" includes not only mammalian cells infected with pathologic viruses but also mammalian cells containing intracellular bacteria or protozoa, e.g., macrophages containing *Mycobacterium tuberculosis, Mycobacterium leper* (leprosy), or *Salmonella typhi* (typhoid fever).

In another embodiment, the pathologically proliferating cells can be pathologic helminths. The term "pathologic helminths" is used herein to refer to pathologic nematodes, pathologic trematodes and pathologic cestodes. More detail on the applicable helminths is set forth at column 12 of U.S. Pat. No. 6,057,367.

In another embodiment, the pathologically proliferating cells can be pathologically proliferating mammalian cells. The term "pathologically proliferating mammalian cells" as used herein means cells of the mammal that grow in size or number in said mammal so as to cause a deleterious effect in the mammal or its organs. The term includes, for example, the pathologically proliferating or enlarging cells causing restenosis, the pathologically proliferating or enlarging cells causing benign prostatic hypertrophy, the pathologically proliferating cells causing myocardial hypertrophy, and proliferating cells at inflammatory sites such as synovial cells in arthritis or cells associated with a cell proliferation disorder.

As used herein, the term "cell proliferative disorder" refers to conditions in which the unregulated and/or abnormal growth of cells can lead to the development of an unwanted condition or disease, which can be cancerous or non-cancerous, for example a psoriatic condition. As used herein, the term "psoriatic condition" refers to disorders involving keratinocyte hyperproliferation, inflammatory cell infiltration, and cytokine alteration. The cell proliferative disorder can be a precancerous condition or cancer. The cancer can be primary cancer or metastatic cancer, or both.

As used herein, the term "cancer" includes solid tumors, such as lung, breast, colon, ovarian, pancreas, prostate, adenocarcinoma, squamous carcinoma, sarcoma, malignant glioma, leiomyosarcoma, hepatoma, head and neck cancer, malignant melanoma, non-melanoma skin cancers, as well as hematologic tumors and/or malignancies, such as leukemia, childhood leukemia and lymphomas, multiple myeloma, Hodgkin's disease, lymphomas of lymphocytic and cutaneous origin, acute and chronic leukemia such as acute lymphoblastic, acute myelocytic, or chronic myelocytic leukemia, plasma cell neoplasm, lymphoid neoplasm, and cancers associated with AIDS.

In addition to psoriatic conditions, the types of proliferative diseases which may be treated using the compositions of the present invention are epidermic and dermoid cysts, lipomas, adenomas, capillary and cutaneous hemangiomas, lymphangiomas, nevi lesions, teratomas, nephromas, myofibromatosis, osteoplastic tumors, and other dysplastic masses, and the like. In one embodiment, proliferative diseases include dysplasias and disorders of the like.

In some embodiments, treating cancer can include a reduction in tumor size, decrease in tumor number, a delay of tumor growth, decrease in metastaic lesions in other tissues or organs distant from the primary tumor site, an improvement in the survival of patients, or an improvement in the quality of patient life, or at least two of the above.

In another embodiment, treating a cell proliferative disorder comprises a reduction in the rate of cellular proliferation, reduction in the proportion of proliferating cells, a decrease in size of an area or zone of cellular proliferation, or a decrease in the number or proportion of cells having an abnormal appearance or morphology, or at least two of the above.

In yet another embodiment, the ADH inhibitors, AKR inhibitors, and/or SNO-CoAR inhibitors can be administered in combination with a second chemotherapeutic agent. In a further embodiment, the second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

In one embodiment, the ADH inhibitors, AKR inhibitors, and/or SNO-CoAR inhibitors can be administered in combination with an agent that imposes nitrosative or oxidative stress. Agents for selectively imposing nitrosative stress to inhibit proliferation of pathologically proliferating cells in combination therapy with the ADH inhibitors, AKR inhibitors, and/or SNO-CoAR inhibitors and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with the ADH inhibitors, AKR inhibitors, and/or SNO-CoAR inhibitors include, for example, L-buthionine-S-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

The the ADH inhibitors, AKR inhibitors, and/or SNO-CoAR inhibitors may also be co-administered with a phosphodiesterase inhibitor (e.g., rolipram, cilomilast, roflumilast, VIAGRA (sildenifil citrate), CLALIS (tadalafil), LEVITRA (vardenifil), etc.), a β-agonist, a steroid, or a leukotriene antagonist (LTD-4). Those skilled in the art can readily determine the appropriate therapeutically effective amount depending on the disorder to be ameliorated.

The ADH inhibitors, AKR inhibitors, and/or SNO-CoAR inhibitors may be used as a means to improve β-adrenergic signaling. In particular, the ADH inhibitors, AKR inhibitors, and/or SNO-CoAR inhibitors alone or in combination with β-agonists could be used to treat or protect against heart failure, or other vascular disorders such as hypertension and asthma. The ADH inhibitors, AKR inhibitors, and/or SNO-CoAR inhibitors can also be used to modulate G protein coupled receptors (GPCRs) by potentiating Gs G-protein, leading to smooth muscle relaxation (e.g., airway and blood vessels), and by attenuating Gq G-protein, and thereby preventing smooth muscle contraction (e.g., in airway and blood vessels).

The therapeutically effective amount for the treatment of a subject afflicted with a disorder ameliorated by NO donor therapy is the ADH, AKR, and/or SNO-CoAR inhibiting amount in vivo that causes amelioration of the disorder being treated or protects against a risk associated with the disorder. For example, for asthma, a therapeutically effective amount is a bronchodilating effective amount; for cystic fibrosis, a therapeutically effective amount is an airway obstruction ameliorating effective amount; for ARDS, a therapeutically effective amount is a hypoxemia ameliorating effective amount; for heart disease, a therapeutically effective amount is an angina relieving or angiogenesis inducing effective amount; for hypertension, a therapeutically effective amount is a blood pressure reducing effective amount; for ischemic coronary disorders, a therapeutic amount is a blood flow increasing effective amount; for atherosclerosis, a therapeutically effective amount is an endothelial dysfunction reversing effective amount; for glaucoma, a therapeutic amount is an intraocular pressure reducing effective amount; for diseases characterized by angiogenesis, a therapeutically effective amount is an angiogenesis inhibiting effective amount; for disorders where there is risk of thrombosis occurring, a therapeutically effective amount is a thrombosis preventing effective amount; for disorders where there is risk of restenosis occurring, a therapeutically effective amount is a restenosis inhibiting effective amount; for chronic inflammatory diseases, a therapeutically effective amount is an inflammation reducing effective amount; for disorders where there is risk of apoptosis occurring, a therapeutically effective amount is an apoptosis preventing effective amount; for impotence, a therapeutically effective amount is an erection attaining or sustaining effective amount; for obesity, a therapeutically effective amount is a satiety causing effective amount; for stroke, a therapeutically effective amount is a blood flow increasing or a TIA protecting effective amount; for reperfusion injury, a therapeutically effective amount is a function increasing effective amount; and for preconditioning of heart and brain, a therapeutically effective amount is a cell protective effective amount, e.g., as measured by troponin or CPK.

The therapeutically effective amount for the treatment of a subject afflicted with pathologically proliferating cells means a ADH, AKR, and/or SNO-CoAR inhibiting amount in vivo which is an antiproliferative effective amount. Such antiproliferative effective amount as used herein means an amount causing reduction in rate of proliferation of at least about 20%, at least about 10%, at least about 5%, or at least about 1%.

The invention is further illustrated by the following examples, which is not intended to limit the scope of the claims.

EXAMPLE

S-nitrosylation, a phylogenetically conserved post-translational modification of proteins that mediates transduction across a broad spectrum of cellular signaling pathways, involves the covalent addition of NO groups to Cys thiols to generate S-nitrosothiols (SNOs). There is increasing evidence that S-nitrosylation is regulated enzymatically. One highly conserved enzyme implicated in regulating S-nitrosylation is represented by S-nitrosoglutathione (GSNO) reductase (GSNOR), which metabolizes the low-molecular-weight SNO, GSNO, employing reducing equivalents from NADH. Because many S-nitrosylated proteins (SNO-proteins) are in equilibrium with GSNO, GSNOR plays a major role in regulating protein S-nitrosylation/denitrosylation.

Coenzyme A (CoA) is an abundant low-molecular-weight thiol that plays an essential role in cells through involvement in over 100 reactions of intermediary metabolism. Although CoA can be S-nitrosylated in vitro, endogenous S-nitrosylation of CoA has not been reported and a role for S-nitroso-CoA (SNO-CoA) in protein S-nitrosylation has not been considered. We wondered whether an enzymatic activity might be involved in regulating the abundance of SNO-CoA and thereby protein S-nitrosylation/denitrosylation (analogous to regulation by GSNOR). We focused initially on an experimentally tractable model eukaryote, the yeast S. cerevisiae.

Materials and Methods
Purification of Yeast and Mammalian SNO-CoA Reductases

SNO-CoA metabolizing activity was purified from a crude extract of yeast cells and bovine kidneys by ammonium sulfate precipitation followed by several steps of column chromatography. The specific activity of NADPH-dependent SNO-CoA reduction was used to assess purification at each step.

Kinetic parameters of Adh6 and AKR1A1

Kinetic analysis was carried out with purified Adh6 and AKR1A1. The reactions contained a fixed concentration of NADPH (100 μM) and several concentrations of SNO-CoA.

Metabolomic Analysis

In extracts of WT and adh6Δ yeast (untreated and following treatment with EtCysNO), mevalonate, CoA and acetyl-CoA were separated and quantified by GC-MS (mevalonate) or LC-MS/MS (CoA, acetyl-CoA).

SNO-RAC Assay and iTRAQ Labeling for Quantification of Protein S-Nitrosylation

Protein S-nitrosylation was assessed by the SNO-RAC assay, and differences in the profile of protein S-nitrosylation in WT versus adh6Δ yeast (under basal growth conditions and upon treatment of cells with EtCysNO) were quantified by iTRAQ labeling.

Preparation of SNO-CoA and Purification of SNO-CoA Reductase from Yeast

SNO-CoA (50 mM stock solution) was freshly prepared for each experiment by combining equal amounts of CoA (0.1 M in 1 N HCl) and sodium nitrite (0.1 M in milliQ water containing 100 μM EDTA and 100 μM DTPA). Stoichiometric yield was verified spectrophotometrically ($\lambda_{max}$ 340 nm, extinction coefficient 0.92 $mM^{-1}$ $cm^{-1}$). This stock solution was stored on ice (SNO-CoA is stable at acidic pH) and aliquots were added directly to lysates; SNO-CoA metabolizing activity was purified from 3 L of yeast cells harvested at $A_{600\ nm}$=5.0. Cells were pelleted and re-suspended in lysis buffer (20 mM bis tris propane, pH 7.0, 50 mM NaCl, 100 μM EDTA, 100 μM DTPA, 1 mM PMSF and protease inhibitor cocktail (Roche)). The crude extract was prepared with a bead-beater (Biospec Products) utilizing glass beads of 0.5 mm diameter, with 15×1 min cycles of beating alternating with 1 min cooling intervals. Following centrifugation at 60,000 g for 1 hr, the supernatant was taken as the starting material for assessment of enrichment of SNO-CoA metabolizing activity. At this and all subsequent stages, enzyme activity was assessed with 200 μM SNO-CoA, 100 μM NADPH in 20 mM bis-tris propane (pH 7) containing 100 μM EDTA and 100 μM DTPA. The supernatant was precipitated with 30% ammonium sulfate followed by centrifugation at 20,000 g, and the resultant supernatant was re-precipitated with 70% ammonium sulfate and pelleted at 20,000 g. The pellet was re-suspended and dialysed against Tris buffer, pH 8.0 at 4° C. The dialyzed extract was applied at 5 ml/min onto a HighPrep Q FastFlow 16×10 mm column equilibrated with 20 mM tris buffer, pH 8.0, and eluted with a linear 0 to 0.3 M NaCl gradient in 20 mM Tris buffer, pH 8.0. Active fractions were pooled, and applied to a 2'-5' ADP-Sepharose 26×120 mm column, equilibrated with Tris buffer pH 8.0, at a flow rate of 2 ml/min, followed by elution with 10 ml of 1 mM $NADP^+$ in 20 mM Tris buffer, pH 8.0. Active fractions were dialyzed against 20 mM tris buffer, pH 8.0. The sample was then applied to a MonoQ GL 5×50 mm column at a flow rate of 1 ml/min followed by elution with a linear 0 to 0.3 M Nacl gradient in 20 mM tris buffer, pH 8.0. Active fractions were pooled, concentrated to less than 200 μl by ultrafiltration, and applied at a flow rate of 0.5 ml/min to a Superdex 200 10×300 mm column equilibrated with PBS. The protein was judged to be pure by SDS-PAGE.

Cloning, Expression and Purification of Recombinant Adh6 and AKR1A1

Yeast ADH6 was amplified from S. cerevisiae genomic DNA with primers: ADH6. ADH6 was cloned into pET21b vector by NdeI and XhoI. Human AKR1A1 was amplified from AKR1A1-encoding cDNA plasmid (Dharmacon; Catalog number MHS6278-202827721). AKR1A1 was cloned into pET21b vector by NdeI and XhoI. Both pET21b-ADH6 and pET21b-AKR1A1 were expressed in Rosetta2(DE3) pLysS E. coli and induced by 100 μM IPTG at $A_{600\ nm}$=0.5. The cells were subsequently grown for 4 h at room temperature. For purification of His-tagged proteins, cell pellets were lysed by sonication in 10 ml of lysis buffer (50 mM phosphate buffer, pH8.0, 600 mM NaCl, 10 mM imidazole, 1 mM PMSF, 1 protease inhibitor tablet (Roche)). The lysates were clarified by centrifugation at 15,000 g for 30 min, followed by incubation with Ni-NTA Agarose (Qiagen) for 1 h. The agarose beads were subsequently incubated with washing buffer (50 mM phosphate buffer, pH8.0, 600 mM NaCl, 30 mM imidazole) for 45 min, and the proteins were eluted by incubation of the beads in elution buffer (50 mM phosphate buffer, pH 8.0, 600 mM NaCl, 250 mM imidazole) for 20 min. Purified proteins were then transferred into PBS by buffer exchange.

Products of Yeast and Mammalian SNO-CoA Reductases

Samples (1 ml) initially contained 20 mM ammonium bicarbonate buffer, 200 µM SNO-CoA and 200 µM NADPH at 25° C. Reactions were initiated by the addition of purified Adh6 or AKR1A1 and allowed to continue until absorbance at 340 nm indicated complete consumption of SNO-CoA (~1 h). Samples were then centrifuged through a 10 kDa cut-off ultrafiltration membrane, and the filtrate was stored at −80° C. until analyzed. For mass spectrometry analysis, samples were diluted 1:2 in HPLC grade acetonitrile. Formic acid was added to the samples at a final concentration of 0.1% (v:v). Samples were injected into a Thermo LTQ Oribtrap XL at a flow rate of 1 uL/min. Mass spectra were acquired from 700-900 m/z. The ion at 799 m/z was isolated and fragmented using CID with a normalized collision energy of 35 and an isolation width of 3.0.

Kinetic Parameters of the Yeast SNO-CoA Reductase

Kinetic analysis was carried out employing assay conditions as above. For $K_m$ determination, reactions (4-5 replicates) were performed with a fixed amount of purified Adh6, 100 µM NADPH and SNO-CoA concentrations of 16-375 µM. Initial rates were calculated from the absorbance decrease at 340 nm using a combined extinction coefficient of 7.06 mM$^{-1}$ cm$^{-1}$ for SNO and NADPH. The $k_{cat}$ was determined at saturating substrate concentrations.

NADPH:SNO-CoA Stoichiometry of Yeast and Mammalian SNO-CoA Reductases

NADPH and SNO-CoA possess essentially identical $\lambda_{max}$ (~340 nm), and the extinction coefficient of NADPH>> SNO-CoA. Therefore, reactions were performed by adding a limiting amount of NADPH (sequential additions of ~100 µM) to Adh6 or AKR1A1 (purified from yeast or kidney lysates) in the presence of excess SNO-CoA (~400 µM) and monitoring the reaction (NADPH consumption) by absorbance spectroscopy until all NADPH was consumed following each addition. The absorbance difference at 340 nm before and after each addition of NADPH was used to calculate the amount of SNO-CoA consumed in the presence of known amounts of NADPH.

SNO-CoA Reductase Activity in Yeast Lysates

Yeast cells were grown to absorbance 600 nm=1.0 in YPD medium (Clontech). Cells were lysed as described above. For enzymatic assay, samples contained both 200 µM SNO-CoA or 100 µM SNO-CoA and 100 µM NADPH. Runs were initiated with the addition of lysate and the absorbance decrease at 340 nm was followed.

Assay for Thiolase Activity

Acetoacetyl-CoA thiolase activity was assayed in the physiological forward direction (2 acetyl-CoA→acetoacetyl-CoA+CoA-SH) by following the formation of CoA-SH with 5,5'-dithiobis(2-nitrobenzoic acid) (DTNB) at 412 nm, as outlined recently for assay of HMG-CoA synthase activity. This approach avoids background absorbance in lysates and interference from added SNO-CoA in the reverse-reaction assay of acetoacetyl-CoA consumption at 300 nm (acetoacetyl-CoA+CoA-SH→2 acetyl-CoA). The assay was performed in 20 mM tris pH 8.0, containing 0.1 mM EDTA and 0.1 mM DTPA. The reaction mixture (1 ml) contained yeast lysate and 100 µM acetyl-CoA. Reaction without the addition of acetyl-CoA was used as background control. In some experiments, various concentrations of GSNO or SNO-CoA were also added. The reaction was monitored following the addition of 0.5 mM DTNB for 3 min at 412 nm. Thiolase activity was determined using rates between 1 and 3 minutes.

Assays for Protein S-Nitrosylation

For analysis in yeast, cells were grown to absorbance 600 nm=1.0 and lysed by bead beating in lysis buffer (20 mM bis-tris propane, pH 7.0, 50 mM NaCl, 100 mM EDTA, 100 µM DTPA, 1 mM PMSF and protease inhibitor cocktail (Roche)). The lysate was centrifuged at 20,000 g for 10 min and the supernatant was adjusted to 1 mg/ml protein and retained for analysis. For analysis of SNO-proteins by mercury-coupled-photolysis-chemiluminescence, samples were processed as previously described. For SNO-RAC, some samples (1 mg/ml) were left untreated or treated for 10 min with 60 µM SNO-CoA±100 µM NADPH. The reaction was stopped by adding 3 volumes of ice-cold acetone, followed by precipitation at −20° C. for 20 min. Precipitates were dissolved in HEN buffer (100 mM HEPES, 1 mM EDTA, 0.1 mM Neucuproine, pH 8.0) containing 0.2% S-methylmethanethiosulfonate and 2.5% SDS and incubated at 50° C. for 20 min with frequent vortexing. Proteins were then re-precipitated with 3 volumes of acetone at −20° C. for 20 minutes and precipitates were dissolved in 1 ml of HEN buffer containing 1% SDS. Proteins were again precipitated with 3 volumes of ice-cold acetone at −20 for 20 minutes and pellets were suspended in 1 ml of fresh HEN buffer/1% SDS. Samples were then incubated with freshly prepared ascorbate (30 mM) and thiopropyl-Sepharose for 4 h, and beads were collected and washed with HEN/1% SDS and 0.1×HEN/1% SDS. Beads were eluted in 0.1×HEN buffer containing 1% SDS and 10% β-meracaptoethanol. Eluates were analyzed by SDS-PAGE followed by Western blotting for erg10 (see below) or, for mass spectrometric analysis, individual lanes were excised from the gel and subjected to trypsin digest prior to processing for LC/MS-MS (see below).

For analysis by SNO-RAC of mammalian SNO-proteins, mouse liver or kidney was homogenized in 50 mM phosphate buffer, pH 7.0, containing 50 mM NaCl, 0.1 mM EDTA, 0.1 mM DTPA, 1 mM PMSF and protease inhibitor cocktail (Roche). The homogenate was centrifuged twice at 20,000 g at 4° C. for 45 min. The supernatant was adjusted to 1 mg/ml total protein and left untreated or treated for 10 min with 60 µM SNO-CoA±100 µM NADPH. The reaction was stopped by adding 3 vol ice-cold acetone, followed by precipitation at −20° C. for 20 mM. SNO-proteins were analyzed by the SNO-RAC method as described above. Eluted SNO-proteins were analyzed by SDS-PAGE followed by Coomassie staining or by Western blotting employing an anti-GAPDH antibody (Abcam ab9485).

Detection of SNO-Erg10

To evaluate S-nitrosylation of Erg10, we employed a yeast strain that expresses the TAP-tagged version of Erg10 under the control of its native promoter (Thermo Scientific; YSC1178-202233637). SNO-proteins were pulled down by SNO-RAC from untreated or SNO-CoA treated lysates by SNO-RAC, and levels of SNO-Erg10 were assessed by Western blotting with an anti-TAP antibody (Thermo Scientific, CAB1001) or by iTRAQ mass spectrometry as described below.

Quantification of SNO Levels in Nitrite-Grown Yeast Cells

Yeast cultures were grown in minimal medium (Yeast Nitrogen Base, MP Biomedicals) containing 0.5% glucose and 5 g/L ammonium sulfate, supplemented with histidine, methionine, uracil (each 20 mg/L) and leucine (100 mg/L). A starting culture was grown aerobically at 30° C. for 24 hours in a shaker, and transferred to an anaerobic glove box (85% $N_2$, 10% $H_2$, 5% $CO_2$). Fresh minimal medium containing 0, 100, or 500 µM sodium nitrite (equilibrated in the glove box) was inoculated with 0.5% of the starter cultures, and grown for 24 hours at ambient temperature (~25° C.). The cultures were removed from the glove box and washed twice in ice-cold water containing 0.1 mM EDTA. Cell pellets were stored at −80° C. until analyses. In time course experiments, cells were grown in the presence of 100 µM nitrite and samples were harvested after 6, 12, and 24 hours.

Metabolic Profiling of CoA-Based Species
Quantification of Mevalonate Levels

Yeast cells grown to mid-log phase (absorbance 600 nm=0.4-0.6) were left untreated or treated with EtCysNO (100 µM) for 2 hrs. Cells were harvested and washed with ice-cold $H_2O$ containing 0.1 mM EDTA or DTPA and stored at −80° C. until further analysis. To the samples, 3 ml of MeOH: $H_2O$ (8:2) was added followed by addition of 100 µl of D4 (1 mM) citrate as an internal standard. Samples were homogenized for 1 minute and 1 ml of the subsequent homogenate was taken and centrifuged at 800 g for 20 minutes. Supernatant was dried by nitrogen gas. 60 µl of N,O-bistrifluoroacetaniide was added to the dried residue and incubated at 70° C. for 30 minutes. Analyses were carried out on an Agilent 5973 mass spectrometer, linked to a 6890 gas chromatograph system equipped with an autosampler. An Agilent VF-5MS capillary column (60 m×0.32 mm×0.25 µm) was used for chromatographic separation. The carrier gas was helium (1 ml/min) with a pulse pressure of 20.1 p.s.i. The injection was in splitless mode. The temperature for both inlet and transfer line was set at 300° C. The ion source and quadrupole temperature were set at 230 and 150° C. The GC temperature program was as follows: start at 80° C., hold for 1 min, and increase by 10° C./min to 300° C., and it remained at 300° C. for 9 min. Mevalonate and internal standard signals were monitored at its nominal m/z with SIM mode. The m/z monitored for mevalonate and internal standard: 349 and 469, respectively. All the masses were measured in Electron Impact Ion Source. The retention times of mevalonate and internal standard are 15.2 and 18.1 minutes, respectively.

Quantification of CoA and Acyl-CoA

Yeast cells grown to mid-log phase (absorbance 600 nm=0.4-0.6) were left untreated or treated with EtCysNO (500 µM) for 2 hrs. Samples of yeast (~1 g) spiked with 0.5 nmol of $[2,2,3,3,3-{}^2H_5]$-propionyl-CoA were extracted for 2 min with 6 ml of methanol/water (1:1) containing 5% acetic acid using a Polytron homogenizer. CoA and acyl-CoAs were assayed as described.

Construction of Adh7Δ and adh6Δadh7Δ Yeast Strains

The entire open reading frame of the ADH7 gene was deleted from haploid wild type (BY4741; Open Biosystems) or adh6Δ strain (Open Biosystems). We used primers to amplify and add ADH7 sequences to both ends of the NatMX cassette by polymerase chain reaction (PCR). Cells stably transfected with NatMX were selected by their resistance to nourseothricin antibiotic (100 µg ml$^{-1}$). Replacement of the ADH7 gene by NatMX4 in the yeast genome was confirmed by PCR using primers. Replacement of the ADH6 gene by KanMX in the adh6Δ and adh6Δadh7Δ strains was confirmed with PCR reactions using primers.

iTRAQ-Coupled SNO-RAC

Extracts of yeast cells were prepared and SNO-RAC (4 mg protein/sample) was carried out as described above. SDS-PAGE gels were Commassie-stained and lanes were separated into eight segments top-to-bottom. Segments were incubated in a 1:1 mixture of acetonitrile and 100 mM ammonium bicarbonate solution for 2-8 hours, followed by addition of 10 mM tris(2-carboxyethyl)phosphine 55 mM iodoacetamide. Gel segments were then dehydrated and rehydrated with acetonitrile and ammonium bicarbonate three times successively, followed by overnight digestion in 50 mM ammonium bicarbonate containing freshly prepared trypsin, 10 ng/µL (Promega, sequencing grade). Peptides were extracted with 60% acetonitrile/0.1% trifluoroacetic acid and extracts were dried under vacuum. For subsequent iTRAQ labeling, peptides were dissolved in 0.5 M triethylammonium bicarbonate, pH 8.5, followed by addition of iTRAQ reagent in ethanol and incubation at room temperature for two hours. Samples were then combined according to experimental design and dried under vacuum.

Liquid Chromatography-Coupled Tandem Mass Spectrometry (LC-MS/MS) Analysis

Prior to analysis by LC-MS/MS, samples were passed through a C18 spin column (Thermo Pierce, Rockford, Ill.) and reconstituted in 0.1% formic acid. Separation of peptides via capillary liquid chromatography was performed using Waters nanoAquity system (Waters Corp., Milford, Mass.). Mobile phase A (aqueous) contained 0.1% formic acid in 5% acetonitrile and mobile phase B (organic) contained 0.1% formic acid in 85% acetonitrile. Separation was achieved using a C18 column (75 mm×20 cm, Waters Corp., Ethylene Bridged Hybrid column #BEH300) through a 150 min gradient of 6% to 45% mobile phase B at a flow rate of 0.30 mL/min. For peptide identification and quantification using iTRAQ reporter ions, MS analysis was performed using a hybrid linear ion trap Orbitrap Velos mass spectrometer (LTQ-Orbitrap Velos, Thermo, Waltham, Mass.). Survey scans were operated at 60,000 resolution with AGC (automatic gain control) target of 1E6. Following three standard CID (collision induced dissociation) fragmentations, HCD (higher-energy collisional dissociation) was carried out for the top three precursor ion fragmentations with a 2 Da isolation window, 40% NCE (normalized collision energy) and a 5,000 signal count threshold. Tandem MS scans with HCD fragmentation were acquired in profile mode with 7,500 resolution and an AGC target of 2E5. Parent proteins were identified with a yeast database (www.yeastgenome.org, *Saccharomyces* Genome Database, Stanford University, Feb. 3, 2011), containing 6,717 protein entries. A decoy database containing the reversed sequences of all proteins was appended to estimate false discovery rate (FDR). Protein identification using Sequest or ProLuCID and DTASelect and quantification using Census were done through the Integrated Proteomics Pipeline (IP2, Integrated Proteomics Applications, Inc. San Diego, Calif.) and checked with MassMatrix. Mass accuracy was limited to 10 ppm for precursor ions and 0.03 Da for product ions, with tryptic enzyme specificity and up to two, missed cleavages. Static modifications included carbamidomethylation on cysteines (57 Da) and iTRAQ-4plex on lysines and N-termini (144 Da). Variable modifications included iTRAQ-4plex on tyrosines (144 Da) and oxidation on methionines (16 Da). DTASelect (33, 34) was applied to generate search results of peptide-to-spectra matches (PSMs) with a maximum FDR of 5%, yielding a protein FDR of less than 2%. Protein quantification based on iTRAQ reporter ions was performed with Census and ratios after median normalization from two or three biological replicates are presented. Peptides without ratios and those that were not replicated in at least two separate experiments were excluded from further analysis. We present fold-change for proteins exhibiting enhanced S-nitrosylation in adh6Δ versus WT yeast (>1.2) only when each of the individual experimental ratios were >1.0 in multiple replicates, with relative standard deviation <35%. p-values were calculated from the identified peptides.

qPCR Analysis of ERG10 Expression

WT and adh6Δ yeast, grown to absorbance 600 nm=0.6, were left untreated or treated with EtCysNO (100 µM) for 2 hr. Total RNA was isolated using a Master Pure Yeast RNA Purification Kit (Epicentre) according to the manufacturer's directions. For reverse transcriptase reactions, 1 µg of total RNA was transcribed to cDNA using iScript Reverse Transcription Supermix for RT-qPCR (Bio-Rad). qPCR was performed with the TaqMan method (using the Roche Universal Probe Library System) on a Step One Plus Real-Time PCR System (Applied Biosystems). Relative expression was calculated using the ΔΔCt method with normalization to GAPDH. To quantify ERG10 expression, probe 86 (Roche) was used. To quantify GAPDH expression, probe 9 (Roche) was used.

Animals

Mouse studies were approved by the Case Western Reserve University IACUC; housing and procedures complied with The Guide for the Care and Use of Laboratory Animals and the AVMA Guidelines on Euthanasia. Tissue was obtained following euthanasia of wild-type and AKR1$^{-/-}$ male mice at 8-12 weeks of age. AKR1A1$^{+/-}$ mice were obtained from Deltagen Inc. (San Mateo, Calif.) and AKR$^{-/-}$ and wild-type breeding pairs were generated. Bovine tissues were obtained from Rockland Immunochemicals Inc. (Gilbertsville, Pa.) and were classified as waste (no IACUC approval required).

Homozygous AKR1A1 Deletion (AKR1A1$^{-/-}$ Mice)

AKR1A1$^{+/-}$ mice were created by insertion of a Lac Z-Neo cassette. Genotyping of subsequently generated AK1A1$^{+/+}$ and AKR1A1$^{-/-}$ mice was performed according to the PCR protocol from Deltagen.

Assay of NADPH-Dependent SNO-CoA Reductase Activity in Mouse

Tissues harvested from AKR1A1$^{+/+}$ and AKR1A1$^{-/-}$ mice were homogenized in lysis buffer (50 mM phosphate buffer, pH 7.0, 150 mM NaCl, 0.1 mM EDTA, 0.1 mM DTPA, 1 mM PMSF and protease inhibitor cocktail (Roche)). Extracts were clarified by centrifugation (20,000 g, 4° C., 45 minutes, X 2), and protein concentration was determined by BCA assay. The NADPH-dependent SNO-CoA reductase activity was determined spectrophotometrically as described above for yeast. Briefly, the assays were performed in 50 mM phosphate buffer, pH 7.0 (containing 0.1 mM EDTA and DTPA) with 0.2 mM SNO-CoA and 0.1 mM NADPH. Reactions were initiated by the addition of lysate and allowed to proceed for 1 min. All assays were performed in duplicate or triplicate.

Purification of Mammalian SNO-CoA Reductase Activity

Bovine kidney tissue (~50 g) was suspended in 100 ml of lysis buffer (50 mM phosphate buffer, pH 7.0, 150 mM NaCl, 1 mM PMSF and protease inhibitor cocktail (Roche)) and lysed in a blender, followed by homogenization with a dounce homogenizer (Wheaton). Following centrifugation×2 at 60,000 g for 45 min, the supernatant was collected. At all stages of purification, enzyme activity was assessed with 0.1 mM SNO-CoA, 0.1 mM NADPH in 50 mM phosphate buffer (pH 7) containing 0.1 mM EDTA and 0.1 mM DTPA. The initial supernatant was precipitated with 30% ammonium sulfate followed by centrifugation at 9,4000 for 30 min at 4° C., and the resultant supernatant was re-precipitated with 60% ammonium sulfate and pelleted at 9,4000 g. The pellet was re-suspended and dialysed against Tris buffer, pH 8.0 at 4° C. The dialyzed extract was applied at 2 ml/min onto a Q Fast Flow (High Prep) column equilibrated with 20 mM Tris buffer, pH 8.0. NADPH-dependent SNO-CoA reductase activity was eluted with a linear 0 to 0.3 M NaCl gradient in 20 mM Tris buffer, pH 8.0. Active fractions were pooled and ammonium sulfate was added to a final concentration of 1M. The sample was then applied onto a phenyl superose (High Prep) column equilibrated with 20 mM tris, pH 8.0 containing 1M ammonium sulfate at a flow rate of 2 ml/min followed by elution using a linear gradient of 0.65 to 0.3M ammonium sulfate in Tris buffer, pH 8.0. Active fractions were pooled and dialyzed overnight against 20 mM Tris buffer, pH 8.0. The dialyzed sample was applied to a MonoQ GL (GE Biosciences) column at a flow rate of 1 ml/min followed by elution with a linear 0 to 0.3 M NaCl gradient in 20 mM Tris buffer, pH 8.0. Active fractions were pooled and ammonium sulfate added to final concentration of 1M. Sample was then applied onto a phenyl sepharose (High Prep) column, pre-equilibrated with 20 mM Tris, pH 8.0 containing 1M ammonium sulfate, at a flow rate of 0.5 ml/min. Active fractions were pooled, concentrated to less than 200 µl by ultrafiltration, and applied at a flow rate of 0.5 ml/min to a Superdex 200 column equilibrated with PBS. Purification was monitored by SDS-PAGE of fractions throughout the purification procedure.

Kinetic Parameters of the Mammalian SNO-CoA Reductase

Kinetic analyses were carried out in 50 mM phosphate buffer, pH 7.0, containing 100 µM EDTA and DTPA. For $K_m$ determination, reactions (2-4 replicates) were performed with a fixed amount of purified AKR1A1, 100 µM NADPH and 2-500 µM SNO-CoA. Initial rates were calculated from the absorbance decrease at 340 nm. The $k_{cat}$ was determined at saturating substrate concentrations.

AKR1A1 Immunodepletion

Ten µg of mouse monoclonal anti-AKR1A1 Ab (Santa Cruz, clone 3B08) or control anti-IgG Ab were bound to 25 µL (packed volume) protein G Sepharose beads (Amersham) in dilution buffer (50 mM phosphate buffer, pH, 7.0, 10 mM NaCl, 0.1 mM EDTA and 0.1 mM DTPA) and the volume brought to 1 ml. Coupling of antibody to beads was done for 1 hr with rotation at 4° C. Antibody-bound beads were washed 3 times with dilution buffer to remove unbound antibodies and collected by centrifugation. Freshly prepared kidney extract (65 µg total protein) from C57B/6 mice (Jackson) was added to the beads and the volume brought to 1 ml with dilution buffer, followed by rotation overnight at 4° C. The sample was centrifuged at 1,000 g for 2 min and the resultant supernatant was retained. NADPH-dependent SNO-CoA reductase activity was assayed with 100 µl aliquots of supernatant. To assess immunodepletion of AKR1A1, 25 µl of supernatant was analyzed by Western blotting.

Results

Adh6 is a SNO-CoA Reductase in Yeast

In extracts of yeast, NADPH, but not NADH, oxidation was greatly enhanced in the presence of SNO-CoA (FIG. 1A, B), consistent with the operation of an NADPH specific SNO-CoA reductase. Addition of SNO-CoA to yeast lysates led to the S-nitrosylation of multiple proteins as demonstrated by the SNO-RAC method and co-addition of NADPH (but not NADH) markedly diminished SNO-protein formation (FIG. 1C). Thus, in yeast, SNO-CoA can serve as a source of NO groups for protein S-nitrosylation that may be regulated by NADPH-dependent SNO-CoA reductase activity. SNO-CoA metabolizing activity was purified from yeast to homogeneity, as assessed by SNO-CoA-dependent NADPH-consumption, and identified as the NADPH-dependent enzyme alcohol dehydrogenase 6 (Adh6; product of the ADH6 gene) (FIG. 1D), a member of the cinnamyl alcohol dehydrogenase family with no previously known physiological role or substrates. NADPH-dependent catabolism of SNO-CoA by Adh6 was confirmed directly with isolated, recombinant Adh6. CoA-sulfinamide was identified by mass spectrometry as the major stable product of SNO-CoA metabolism (FIG. 2A), confirming a reductase mechanism that produces an S—(N-hydroxy)-CoA intermediate. Kinetic analysis gave, with SNO-CoA as substrate, a $K_m$ of 180.5±16.8 µM and an estimated $k_{cat}$ of 2596.5±110.7 $min^{-1}$ (FIG. 2B), and a stoichiometry with co-substrate NADPH of 1:1 (FIG. 2C). The catalytic efficiency ($k_{cat}/K_m$) of Adh6 (for substrate SNO-CoA) compares closely with that of microbial GSNO reductase (for substrate GSNO), supporting physiological relevance (and as for GSNOR, a relatively high $K_m$ is consistent with a homeostatic functional role). Importantly, Adh6 was specific for SNO-CoA versus GSNO or S-nitroso-cysteine (CysNO), and oxidized CoA or CoA-glutathione mixed disulfide (FIG. 2D). Adh6 is the principal source of SNO-CoA metabolizing activity, because genetic deletion of ADH6 (adh6Δ) resulted in −80% decrease in SNO-CoA-consuming activity in lysates, whereas deletion of closely homologous ADH7 had no effect (FIG. 2E).

SNO-CoA-Mediated Protein S-Nitrosylation is Regulated by Adh6

In yeast, GSNOR-regulated denitrosylation of SNO-proteins (coupled to metabolism of GSNO) protects against nitrosative stress imposed by exogenous NO, as demonstrated by enhanced susceptibility to nitrosative challenge in GSNOR-null cells. In contrast, deletion of ADH6 did not affect the growth response to nitrosative stress, suggesting distinct functions for SNO-CoA and GSNO. To reveal possible roles for SNO-CoA, and in particular to explore a possible role for SNO-CoA in metabolic signaling, we employed a mass spectrometry-based approach to identify substrates of SNO-CoA-mediated, Adh6-regulated protein S-nitrosylation. We treated lysates of wild-type (WT) yeast with SNO-CoA (which is not cell-permeable) and treated intact WT and adh6Δ yeast with the cell-permeable S-nitrosylating agent, S-nitroso-cysteine ethyl ester (EtCysNO). NO groups originating from EtCysNO will distribute among intracellular SNOs, forming SNO-CoA, and as shown in FIG. 3A and detailed below, there is substantial overlap between the sets of proteins S-nitrosylated by EtCysNO or SNO-CoA. SNO-proteins were captured by SNO-RAC and tryptic peptides were quantified by iTRAQ and LC-MS/MS.

Treatment of lysates with SNO-CoA (60 µM, 10 min) resulted in the identification of 345 SNO-proteins (FIG. 3A). SNO-CoA-induced protein S-nitrosylation was greatly attenuated in WT lysates by addition of NADPH, and this attenuation was partially eliminated in adh6Δ lysates (FIG. 3B), confirming regulation by Adh6 of SNO-CoA-mediated protein S-nitrosylation. Similarly, treatment of intact cells with EtCysNO (100 µM, 2 hr) resulted in the identification of 103 SNO-proteins (FIG. 3C), and iTRAQ analysis revealed that ADH6 deletion resulted in significantly enhanced S-nitrosylation of 15 of those proteins (FIG. 3C). Notably, 10 of 15 proteins exhibiting Adh6-dependent enhanced S-nitrosylation after EtCysNO treatment of intact cells were identified as SNO-CoA substrates in lysates (FIG. 3C). The majority of substrates for Adh6-regulated S-nitrosylation were identified as metabolic enzymes (FIG. 3C), including Erg10 (acetoacetyl-CoA thiolase) (FIG. 3C), which plays a key role in CoA-dependent sterol biosynthesis, as well as several enzymes influencing acyl-CoA levels (vida infra). We further confirmed that the enhanced S-nitrosylation of Erg10 in adh6Δ yeast did not reflect changes in Erg10 abundance.

Endogenous S-Nitrosylation and Regulation by Adh6 of Erg10 Activity

In yeast, as in bacteria, NO is generated by respiratory enzymes that reduce nitrite and/or nitrate (i.e., NO is produced in the absence of a nitric oxide synthase (NOS)). However, endogenous protein S-nitrosylation has not been described previously in yeast and in general the role of yeast NO is unknown. Our analysis revealed constitutive protein S-nitrosylation in yeast under basal conditions with both SNO-RAC (FIG. 3C) and mercury-coupled photolysis/chemiluminescence (FIG. 3E), and identified 51 endogenous SNO-proteins. Notably, 37/51 endogenous substrates were also identified as targets of exogenous SNO-CoA. In addition, five endogenous SNO-proteins exhibited enhanced basal S-nitrosylation in the absence of Adh6 (FIG. 3C) and three of these substrates were among the set identified as targets of exogenous SNO-CoA, including Erg10 thiolase. Acetoacetyl-CoA thiolase has also been identified by proteomic analysis as an endogenous SNO-protein in mammals. Both endogenous and exogenous SNO-CoA-mediated S-nitrosylation of Erg10 were confirmed directly by SNO-RAC analysis of untreated extracts and extracts treated with SNO-CoA (50 µM) (FIG. 3F). Nitrite-dependent NO production by yeast mitochondria is enhanced under hypoxic conditions. Supplementation of intact yeast with nitrite (100 µM) under hypoxia to enhance endogenous NO production led to the progressive accumulation of SNO-proteins as assessed by photolysis/chemiluminescence (FIG. 4A), and these increases in endogenous SNO-protein levels were substantially greater in adh6Δ versus WT yeast (FIG. 4B). Thus, collectively, these data support a role for SNO-CoA in endogenous protein S-nitrosylation in yeast that is regulated by Adh6 and indicate that SNO-CoA-mediated, Adh6-regulated protein S-nitrosylation is coupled to endogenous NO production.

To illustrate regulation of metabolism through endogenous SNO-CoA-mediated protein S-nitrosylation, we focused on Erg10 (identified as a substrate for Adh6-regulated S-nitrosylation by both endogenous and exogenous SNO-CoA; FIG. 3C, F). Nitrite supplementation of hypoxic yeast cultures to enhance endogenous S-nitrosylation resulted in inhibition of acetoacetyl-CoA thiolase activity (FIG. 4C), and this inhibition was significantly greater in adh6Δ versus WT cells (FIG. 4C), implicating SNO-CoA. Treatment of normoxic cultures with EtCysNO (100 µM) revealed similar regulation of thiolase activity by Adh6 (FIG. 4C), specifically implicating SNO-CoA in the inhibitory effects of EtCysNO (recall that Adh6 does not metabolize CysNO; FIG. 2D). Moreover, we verified in yeast extracts and with purified protein ($IC_{50}$=4 µM) that SNO-CoA potently inhibited Erg10 thiolase activity (FIG. 4D, E), whereas notably, neither GSNO (FIG. 4D) nor succinyl-CoA (a CoA analogue) (FIG. 4E) had a significant effect. That is, thiolase is selectively inhibited by SNO-CoA and thus, the inhibition of thiolase that is coupled to endogenous NO production or exogenous nitrosative stress (and regulated by the SNO-CoA reductase Adh6) is likely to be selectively mediated by SNO-CoA.

Erg10 is a critical component of the CoA-based mevalonate pathway for sterol biosynthesis; yeast lacking Erg10 are mevalonate auxotrophs. To establish a functional corollary of thiolase inhibition by SNO-CoA, we carried out metabolomic analyses in WT versus adh6Δ yeast, focused on components of CoA-based metabolism including mevalonate. Metabolomic analysis demonstrated that treatment with EtCysNO, under conditions employed to demonstrate SNO-CoA-mediated Erg10 S-nitrosylation (FIG. 3A, C), resulted in a significant decrease of mevalonate levels in adh6Δ yeast, but not in WT yeast (FIG. 4F), consistent with inhibition of Erg10 activity by SNO-CoA (FIG. 4I). As a measure of the effect of Erg10 inhibition by SNO-CoA on mevalonate biosynthesis, mevalonate levels in EtCysNO-treated adh6Δ yeast were similar to the levels observed in yeast harboring the erg10-DAmp gene (FIG. 4F), which codes for a form of Erg10 that exhibits ~50% reduction in thiolase activity. In addition, metabolomic analysis revealed that treatment with EtCysNO resulted in large decreases in free CoA (FIG. 4G), consistent with formation of SNO-CoA (which escapes detection at physiological concentrations, as is the case for other unstable, short-lived SNOs, including GSNO and CysNO; note that SNO-CoA is not regenerated to CoA by Adh6). However, whereas levels of precursor CoA and downstream product mevalonate were decreased, levels of acetyl-CoA were increased and this increase was significantly larger in adh6Δ versus WT cells (FIG. 4H). Metabolic blockade of acetyl-CoA utilization though Erg10, which would also contribute to decreased levels of CoA, may play a role in enhancement of acetyl-CoA levels (FIG. 4I). However, it is well known that acetyl-CoA generation is governed in large part by fatty acid (β-) oxidation, which is enhanced by S-nitrosylation, and by the pyruvate dehydrogenase multi-enzyme complex, and we identified some components of those mechanisms as SNO-proteins, including components of the pyruvate dehydrogenase complex that exhibited Adh6-regulated S-nitrosylation (FIG. 3C). Thus, Adh6-regulated S-nitrosylation may potentially signal through modification of multiple components of CoA-related metabolic pathways. Finally, it is important to note that constitutive levels of acetyl-CoA were increased significantly in adh6Δ versus WT yeast in the absence of exogenous SNO (FIG. 4H), indicating directly metabolic regulation by endogenous SNO-CoA. Adh6 is thus a newly discovered SNO-CoA reductase that influences CoA metabolism in yeast.

AKR1A1 is a SNO-CoA Reductase in Mammals

Adh6 is unique to yeast (phylum Ascomycetes). However, the generality of our findings is indicated by our discovery of NADPH-dependent SNO-CoA reductase activity across a phylogenetic spectrum from bacteria to mammals (FIG. 5A, B; see also FIG. 6D). As in yeast, addition of SNO-CoA to lysates of mouse tissues led to the S-nitrosylation of multiple proteins and co-addition of NADPH (but not NADH) markedly diminished SNO-protein formation (FIG. 5C). Employing an approach identical in all significant respects to that utilized in the analysis of Adh6 in yeast, we purified (from bovine liver and kidney) the mammalian SNO-CoA reductase and identified it as aldo-keto reductase 1A1 (AKR1A1) (FIG. 5D). AKR1A1 is the founding member of the AKR superfamily and orthologs are present across the vertebrate phylum. However, the physiological role of AKR1A1 remains unknown, with the exception of a role in vitamin C synthesis that has been demonstrated in the mouse, although many mammals including humans do not synthesize vitamin C. Mass spectrometric analysis demonstrated that the reductive mechanism (involving hydride transfer; FIG. 6A) and product (CoA-sulfinamide) of AKR1A1 operating as a SNO-CoA reductase were identical to those of yeast Adh6. Kinetic analysis gave, with SNO-CoA as substrate, a $K_m$ of 20.5±1.8 μM and an estimated $k_{cat}$ of 627±23.76 min$^{-1}$ (FIG. 6B) and, as for Adh6, a stoichiometry with co-substrate NADPH of 1:1 (FIG. 6C). AKR1A1 and Adh6 are evolutionarily unrelated, and are therefore functional analogs. The existence of evolutionarily unrelated functional analogs in yeast and mammals indicates strongly that SNO-CoA reductase activity is biologically significant.

Transgenic mice bearing an unconditional knockout of AKR1A1 were generated to demonstrate that AKR1A1 is the predominant source of NADPH-dependent SNO-CoA reductase activity in mammalian tissue (FIG. 6D), and these results were confirmed by immunodepletion of AKR1A1 from tissue extracts. To illustrate regulation by AKR1A1 of endogenous SNO-CoA-mediated protein S-nitrosylation, we focused as an exemplar on glyceraldehyde 3-phosphate dehydrogenase (GAPDH). GAPDH is best characterized among the multitude of mammalian metabolic enzymes that are regulated by S-nitrosylation, which includes both loss- and gain-of-function roles for SNO-GAPDH in metabolic regulation, metabolic inflammation and glycolysis. Further, GAPDH is among the set of SNO-proteins in which S-nitrosylation is not regulated through coupling to GSH/GSNO (i.e., is independent of GSNOR) and which we find is mediated effectively by SNO-CoA. Analysis by SNO-RAC in AKR1A1-null and WT tissues, followed by either Western blotting (FIG. 6E) or iTRAQ-mass spectrometry (FIG. 6F) showed that SNO-GAPDH levels are enhanced substantially in the absence of AKR1A1. Thus, SNO-CoA is likely a principal low-molecular-weight SNO that exists in equilibrium with SNO-GAPDH to regulate GAPDH S-nitrosylation/denitrosylation, with AKR1A1 serving to control that equilibrium.

Our results reveal a new functional class of enzymes, SNO-CoA reductases, and establish a phylogenetically conserved role for this enzymatic machinery in the regulation of protein S-nitrosylation. Our findings include the first demonstration of endogenous S-nitrosylation in yeast, and the identification of SNO-CoA as a novel signaling molecule. Endogenous SNOs in a variety of low-molecular-weight and protein forms may purvey NO bioactivity. However, assignments of individual roles for ephemeral small-molecular-weight SNOs in cellular function can only be achieved through the identification of dedicated enzymes that metabolize individual SNOs (it is important to appreciate in this regard that no enzymes have been found to metabolize NO in mammals that would allow assignment of function to NO that is independent of SNOs). Here, as in previous analyses of the role of GSNO in protein S-nitrosylation based on genetic manipulation of the GSNO metabolizing enzyme GSNOR, we employed genetic manipulation of novel, specific SNO-CoA metabolizing enzymes to establish a role for SNO-CoA in NO-based cellular signaling.

Our findings demonstrate that, in cells producing or otherwise exposed to NO, SNO-CoA may serve as a source of NO groups for protein S-nitrosylation and that protein S-nitrosylation regulated by SNO-CoA reductases may provide a mechanism for metabolic regulation by NO. In particular, in yeast, regulation by the dedicated SNO-CoA reductase, Adh6, of Erg10 S-nitrosylation demonstrates a previously unsuspected locus of control of sterol metabolism. Adh6 may thereby protect yeast against sterol auxotrophy caused by endogenous or exogenous (e.g., host-derived or soil) NO. More generally, the disruption of CoA homeostasis (e.g., CoA depletion) that we observed upon treatment of yeast with an S-nitrosylating agent may contribute to nitrosative stress induced by exogenous NO (or iNOS induction in mammalian cells), and a possible protective role for Adh6 may entail an effective mechanism to regenerate CoA from CoA sulfinamide (FIG. 2). The regulation in mammals by a cognate SNO-CoA reductase of GAPDH S-nitrosylation, extensively characterized as an exemplar of metabolic signaling by NO, supports the prediction that SNO-CoA may convey metabolic signals more broadly. Further, S-nitrosylated GAPDH has been shown recently to function as an S-nitrosylase and thereby to serve as an important regulator of protein acetylation within the nucleus that impacts cellular metabolism. Thus, our findings suggest that S-nitrosylation and acetylation provide distinct CoA-based mechanisms for post-translational protein modification that will together exert a broad functional purview in most or all cells, with implications for both physiology and disease.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

I claim:

1. A method of treating disorders associated with NO/SNO deficiency or benefiting from increased SNO in a subject in need thereof, the method comprising:

administering to the subject having a disorder associated with NO/SNO deficiency or benefiting from increased SNO an aldo-keto reductase (AKR) inhibitor at an amount(s) effective to promote S-nitrosylation of proteins in the subject, wherein the AKR inhibitor is an AKR1A1 inhibitor, wherein the AKR1A1 inhibitor is a compound selected from the group consisting of:

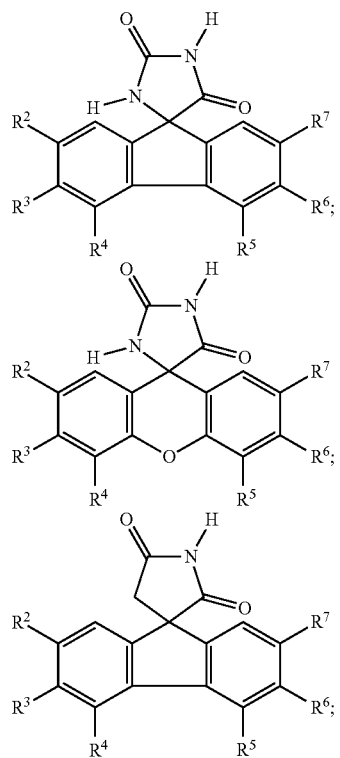

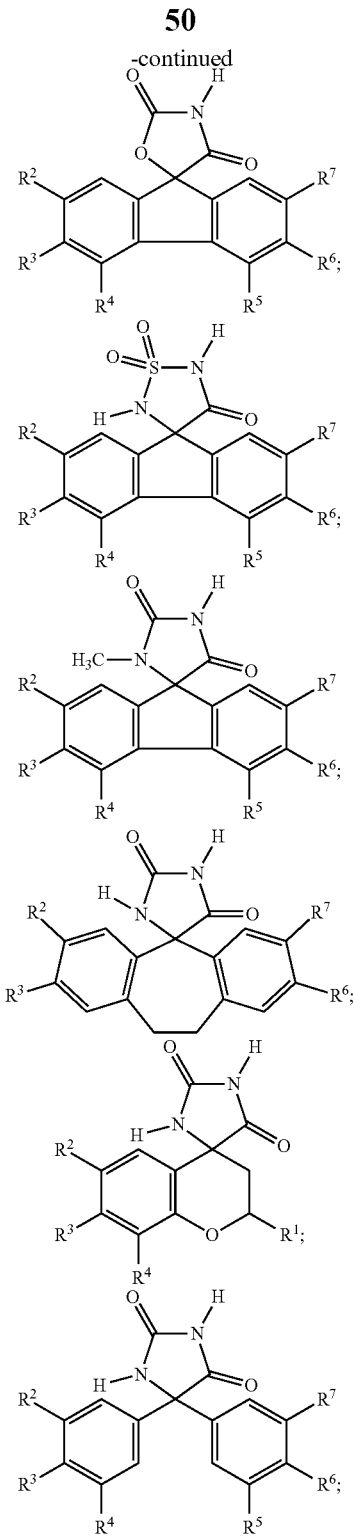

and a pharmaceutically acceptable salt thereof;

each $R^1$, $R^2$, $R^3$, $R^4$, $R^5$, $R^6$, and $R^7$ are the same or different and are one or more substituent selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl (—(CO)—NH($C_1$-$C_{24}$ alkyl)), arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_6$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_6$-$C_{20}$ arylsulfinyl, $C_1$-$C_{24}$ alkylsulfonyl, $C_6$-$C_{20}$ arylsulfonyl, sulfonamide, phosphono, phosphonato, phosphinato, phospho, phosphino, polyalkyl ethers, and combinations thereof; and wherein the disorders comprise at least one of cerebrovascular ischemia, myocardial ischemia, organ ischemia, tissue ischemia, critical limb ischemia (CLI), embolic brain ischemia, ischemic cardiomyopathy, renal ischemia, pulmonary ischemia, or intestinal ischemia.

2. The method of claim 1, wherein the AKR1A1 inhibitor includes 2,7-Difluoro-2'H,5'H-spiro[fluorene-9,4'-imidazolidine]-2',5'-dione (imirestat).

3. The method of claim 1, wherein the AKR1A1 inhibitor has an AKR1A1 $IC_{50} \leq 25$ nM and an AKR1B1/AKR1A1 $IC_{50} \leq 300$ nM.

4. The method of claim 1, wherein the disorders comprise at least one of myocardial ischemia and renal ischemia.

5. A method of treating a subject at risk of ischemia/reperfusion-induced myocardial infarction (MI/R) comprising:

administering to the subject prior to MI/R an AKR1A1 inhibitor at an amount effective to promote S-nitrosylation of proteins and to provide a cell protective effect as measured by a reduction of troponin level post myocardial infarction in the subject, wherein the AKR1A1 inhibitor is a compound selected from the group consisting of:

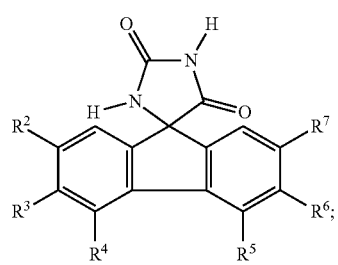

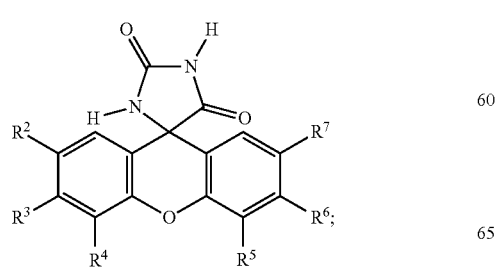

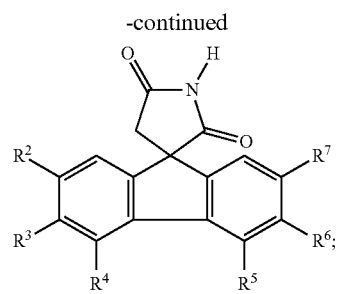

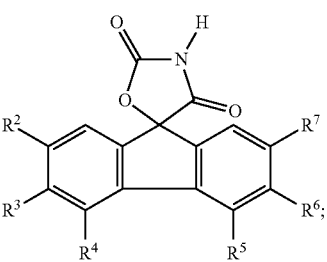

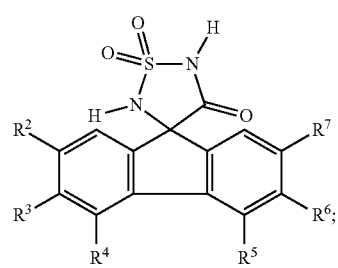

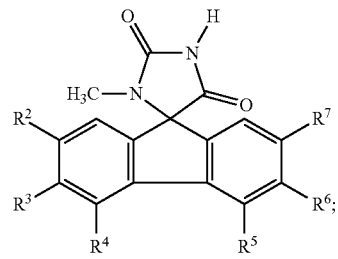

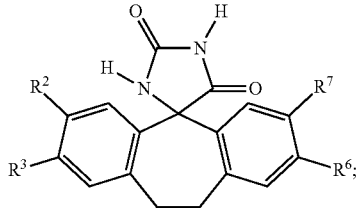

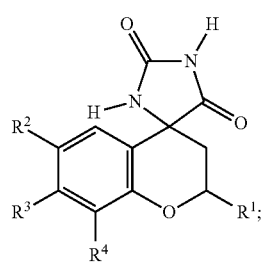

-continued

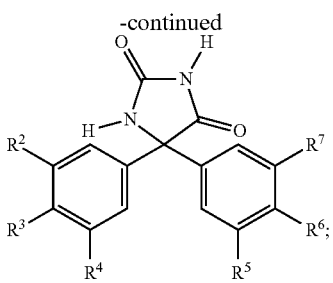

and a pharmaceutically acceptable salt thereof;

each $R^1$, $R^2$, $R^3$, $R^4$, $R^5$, $R^6$, and $R^7$ are the same or different and are one or more substituent selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl (—(CO)—NH($C_1$-$C_{24}$ alkyl)), arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_6$-$C_{20}$ aryl amino, $C_2$-$C_{24}$ alkylamido, $C_6$-$C_{20}$ arylamido, sulfanamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_6$-$C_{20}$ arylsulfinyl, $C_1$-$C_{24}$ alkylsulfonyl, $C_6$-$C_{20}$ arylsulfonyl, sulfonamide, phosphono, phosphonato, phosphinato, phospho, phosphino, polyalkyl ethers, and combinations thereof.

6. The method of claim 5, wherein the AKR1A1 inhibitor is 2,7-Difluoro-2'H,5'H-spiro[fluorene-9,4'-imidazolidine]-2',5'-dione (imirestat).

7. A method of treating disorders associated with NO/SNO deficiency or benefiting from increased SNO in a subject in need thereof, the method comprising:
administering to the subject having a disorder associated with NO/SNO deficiency or benefiting from increased SNO an AKR1A1 inhibitor at an amount effective to promote S-nitrosylation of proteins in the subject, wherein the AKR1A1 inhibitor is 2,7-Difluoro-2'H, 5'H-spiro[fluorene-9,4'-imidazolidine]-2',5'-dione (imirestat); and wherein the disorders comprise at least one of myocardial ischemia and renal ischemia.

* * * * *